(12) United States Patent
Dalkara et al.

(10) Patent No.: US 11,390,866 B2
(45) Date of Patent: Jul. 19, 2022

(54) PROMOTERS AND USES THEREOF

(71) Applicants: SORBONNE UNIVERSITE, Paris (FR); INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); FRIEDRICH MIESCHER INSTITUTE FOR BIOMEDICAL RESEARCH, Basel (CH)

(72) Inventors: Deniz Dalkara, Alfortville (FR); Serge Picaud, Avon (FR); Melissa Desrosiers, Alfortville (FR); Jose-Alain Sahel, Paris (FR); Jens Duebel, Paris (FR); Alexis Bemelmans, Chatou (FR); Botond Roska, Oberwil (CH)

(73) Assignees: SORBONNE UNIVERSITÉ, Paris (FR); INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); FRIEDRICH MIESCHER INSTITUTE FOR BIOMEDICAL RESEARCH, Basel (CH)

( * ) Notice: Subject to any disclaimer, the term of this patent is extended or adjusted under 35 U.S.C. 154(b) by 292 days.

(21) Appl. No.: 15/781,191

(22) PCT Filed: Dec. 5, 2016

(86) PCT No.: PCT/EP2016/079755
§ 371 (c)(1),
(2) Date: Jun. 4, 2018

(87) PCT Pub. No.: WO2017/093566
PCT Pub. Date: Jun. 8, 2017

(65) Prior Publication Data
US 2018/0355354 A1    Dec. 13, 2018

(30) Foreign Application Priority Data
Dec. 4, 2015   (EP) .................................... 15306932

(51) Int. Cl.
| | | |
|---|---|---|
| C12N 15/113 | (2010.01) | |
| C12N 15/85 | (2006.01) | |
| A61P 25/28 | (2006.01) | |
| A61P 25/02 | (2006.01) | |
| A61P 27/00 | (2006.01) | |
| A61K 31/7105 | (2006.01) | |
| A61K 31/711 | (2006.01) | |
| A61K 48/00 | (2006.01) | |

(52) U.S. Cl.
CPC .......... *C12N 15/113* (2013.01); *A61K 31/711* (2013.01); *A61K 31/7105* (2013.01); *A61K 48/0058* (2013.01); *A61P 25/02* (2018.01); *A61P 25/28* (2018.01); *A61P 27/00* (2018.01); *C12N 15/85* (2013.01); *C12N 2750/14132* (2013.01); *C12N 2750/14143* (2013.01); *C12N 2750/14145* (2013.01); *C12N 2840/105* (2013.01)

(58) Field of Classification Search
CPC .................. C12N 15/113; C12N 15/85; C12N 2750/14132; C12N 2750/14143; C12N 2750/14145; C12N 2840/105; A61P 25/28; A61P 25/02; A61P 27/00; A61K 31/7105; A61K 31/711; A61K 48/0058
See application file for complete search history.

(56) References Cited

U.S. PATENT DOCUMENTS 8,242,093 B2 * 8/2012 Bartus .................. A61K 48/005
514/44 R

FOREIGN PATENT DOCUMENTS

| WO | WO 2007/009755 | 1/2007 |
| WO | WO 2015/143418 | 9/2015 |

OTHER PUBLICATIONS

Chaffioli et al "A New Promoter Allows Optogenetic Vision Resoration with Enhanced Sensitivitly in Macaque Retina" (Molecular Therapy 2017 vol. 25 No. 11, Nov. 2017; pp. 2546-2560). (Year: 2017).*
Lu, A. et al. "Molecular mechanisms for aberrant expression of the human breast cancer specific gene 1 in breast cancer cells: control of transcription by DNA methylation and intronic sequences" *Oncogene*, Aug. 23, 2001, pp. 5173-5185, vol. 20, No. 37.
Surgucheva, I. et al. "γ-Synuclein: Cell-Type-Specific Promoter Activity and Binding to Transcription Factors" *Journal of Molecular Neuroscience*, May 23, 2008, pp. 267-271, vol. 35.
Surgucheva, I. et al. "γ-Synuclein as a marker of retinal ganglion cells" *Molecular Vision*, Aug. 22, 2008, pp. 1540-1548, vol. 14.
Written Opinion in International Application No. PCT/EP2016/079755, dated Mar. 10, 2017, pp. 1-6.
Ninkina, N. N. et al. "Organization, expression and polymorphism of the human persyn gene" *Human Molecular Genetics*, 1998, pp. 1417-1424, vol. 7, No. 9.

* cited by examiner

*Primary Examiner* — Catherine S Hibbert
(74) *Attorney, Agent, or Firm* — Saliwanchik, Lloyd & Eisenschenk

(57) ABSTRACT

The present invention relates to a nucleic acid sequence derived from the regulatory region of the human gamma-synuclein gene and having a promoter activity in retinal ganglion cells. The present invention also relates to expression cassettes or vectors comprising said promoter operably linked to a nucleic acid sequence encoding a polypeptide of interest as well as viral particles or host cells comprising said expression cassette or vector. The present invention also relates to the use of said expression cassettes, vectors, viral particles or cells in the treatment of ocular disease, in particular ocular disease associated with retinal ganglion cell or photoreceptor cell degeneration.

28 Claims, 15 Drawing Sheets
Specification includes a Sequence Listing.

PROMOTERS AND USES THEREOF

CROSS-REFERENCE TO RELATED APPLICATION

This application is the U.S. national stage application of International Patent Application No. PCT/EP2016/079755, filed Dec. 5, 2016.

The Sequence Listing for this application is labeled "Seq-List.txt" which was created on Apr. 30, 2018 and is 3 KB. The entire content of the sequence listing is incorporated herein by reference in its entirety.

FIELD OF THE INVENTION

The present invention relates to the field of medicine, in particular to the treatment and prevention of a disease associated with retinal ganglion cell or photoreceptor cell degeneration.

BACKGROUND OF THE INVENTION

One can divide the retina in two parts, the retinal pigment epithelium (RPE) and the neurosensory retina. RPE is actively involved in maintaining neurosensory retina function. Neurosensory retina is organized as a neural network including photoreceptors and retinal ganglion cells (RGC). Photoreceptors convert light information in electrical information directed to RGCs, the latter being responsible for transmission of visual information from the retina to the visual cortex. Between these different cellular types, we can also find cells having regulatory functions such as horizontal cells that induce a negative feedback allowing adaptation of the retina response to various conditions of light intensity and increase of the contrast information.

RGCs are mainly glutamatergic neurons, which are located in the inner surface (the ganglion cell layer) of the retina. Their axons form the optic nerve. About 15 to 20 several types of RGC exist. RGCs play a key role in the vision process and RGC dysfunction or degeneration may lead to blindness.

A wide variety of pathologies, called optic neuropathies, are caused by a primary deficit of RGCs. Some of which are genetic diseases, such as Leber hereditary optic neuropathy (LHON) caused by mutations of mitochondrial genes. However, acquired optic neuropathies are much more prevalent, such as glaucoma that is the second most important cause of blindness in developed countries, affecting 70 million people worldwide.

A targeted expression in ganglion cells of healthy version of the gene responsible for these diseases, or gene encoding neuroprotection factors, may allow treatment of these optic neuropathies. It is therefore essential to be able to obtain strong and specific gene expression in these cells to provide gene-therapy.

Furthermore, RGCs may constitute a treatment target without being directly implicated in the degenerative process. For example, RGCs persist for extended periods after photoreceptor degeneration in diseases where photoreceptors are lost due to inherited (i.e. Retinitis Pigmentosa) or acquired disease thus constituting targets for treatments to reanimate the retina using optogenetic tools. In this context, RGCs are the cellular targets independent of the degenerating cells where the expression of a photosensitive protein in a strong and restricted manner is essential to the success of vision restoration.

There is also a great interest in studying RGC function as their size, shape and projections of each type of RGC is distinctive, and they are thought to play quite different and possibly independent roles in visual function, but at present relatively little is known about this question. A promoter sequence that can drive gene expression in these cells will allow identifying or tracking RGCs, monitoring their activity through expression of genetically encoded voltage or calcium sensitive proteins (i.e. GCaMP).

In previous state-of-the-art, gene expression in the RGCs has been obtained through the use of either ubiquitous promoters or promoters specific to tissue(s). Ubiquitous promoters afford a strong but unrestricted gene expression pattern in tissues. Ubiquitous eukaryotic promoters are either derived from chicken beta actin (CBA) gene or phosphoglycerated kinase (PGK) or the promoter of the elongation factor 1 alpha (EF1alpha). Other ubiquitous promoters, of viral origin, include those derived from the cytomegalovirus (CMV) or synthetic promoter sequences such as CAG. However, it has been demonstrated that regulation of the CMV promoter is dependent on many cell signaling pathways capable of altering the expression of the transgene. Furthermore, these promoters are not restrictive of a given cell type and lead to expression in all cells into which they are delivered such as retinal pigment epithelium (RPE), Müller glial cells of the retina and other ocular tissues outside the retina such as the ciliary body, iris, cornea etc.

Gene expression restricted to retinal cells has been obtained using tissue-specific promoters leading to expression in RPE or photoreceptors. Promoters such as those based on RPE65, VMD2 and OA1 give rise to gene expression in the RPE cells whereas promoters of human (RK) or bovine (RHO) rhodopsin kinase or promoter of mouse opsin (mOP) lead to expression restricted to photoreceptors. These promoters are restrictive towards the retina but are not efficient in RGCs.

Several proteins have been described as being expressed in RGCs of the retina. Among these proteins, Thy1-1 (thymocyte antigen1-1) or Brn3-a proteins are conventionally used as markers of ganglion cells. However, Thy1-1 protein is not specific to RGCs since it is also expressed in macrophages and microglial cells. Furthermore, both Thy-1 and Brn3-a are only expressed in a subset of ganglion cells. Thus, the promoter regions of these markers would not allow a specific expression of a transgene in the whole ganglion cell population.

Recently several promoter sequences leading to restricted expression in retinal ganglion cells after delivery to the retina have been described. One sequence of 2.8 kB, based on human connexin36 (cx36), drives expression in a specific sub-type of RGCs in mice and in peri-foveaolar RGCs in non-human primates. (Yin et al., IOVS, 2011; 52(5):2775-8; Dalkara et al., Sci Trans Med, 2013; 5(189):189ra76). Simpson and colleagues have described other promoter elements of above 3.3 kB (Ple25, Ple53 and Ple67), driving expression in RGCs (de Leeuw et al., Mol Ther Meth and Clin Dev, 2014; 1:5).

The gamma-synuclein gene (SNCG) has also been described as expressed in the retina, and more particularly, a colocalization of gamma-synuclein with Brn3-protein in human and rodent RGCs has been described (Surgucheva et al, Mol Vis, 2008, 14, 1540-8). However, the authors also noted immunoreactivity for gamma-synuclein in retinal plexiform cells as well as in cells non-identified by authors and that do not express Brn3-a protein. Furthermore, the authors showed in non-RGC cell lines, that the gamma-synuclein promoter activity is supported by a 2,195-bp fragment of the γ-synuclein gene including 1,260 bp of the noncoding 5'flanking region upstream of the start ATG codon, as well as exon 1 and intron 1 which were described as having an essential role in regulating the expression of the SNCG gene, again in the non-RGC cell lines studied (Surgucheva et al., J Mol Neurosci, 2008, 35: 267-71).

Many recombinant viral vectors were described as allowing efficient gene transfer in vivo for gene therapy applications. Among them, adeno-associated virus (AAV) is likely to be a key delivery mechanism due to its non-pathogenic, non-insertional and low immunogenicity characteristics. In addition, AAV has been described as allowing very efficient transduction in rodent RGCs. Indeed, it has been shown by different research teams that intravitreal injection of an AAV serotype 2 (AAV2) or a tyrosine mutated form thereof, in mice led to very efficient expression of a reporter gene in the RGCs (Petrs-Silva et al., Mol Ther. 2009 March; 17(3):463-71; Petrs-Silva et al., Mol Ther. 2011 February; 19(2):293-301). However, because of its small size, the DNA payload of AAV is severely limited and is not compatible with the use of large promoters such as RGC specific promoters described in the prior art.

Consequently, there is a strong need to develop a compact promoter allowing strong, stable and specific expression of a transgene in RGCs and being particularly suitable for gene transfer using AAV vectors.

SUMMARY OF THE INVENTION

The inventors herein provide a new transcriptional promoter having a short length and thus being suitable for use in combination with AAV vectors, and that can drive high-level gene expression specifically in retinal ganglion cells (RGCs).

Accordingly, in a first aspect, the present invention relates to an isolated nucleic acid having a promoter activity in retinal ganglion cells, wherein said nucleic acid has a length of less than 1.5 kb and comprises a sequence selected from the group consisting of
   the sequence of SEQ ID NO: 1,
   a sequence having at least 80% identity to SEQ ID NO:1,
   a sequence comprising at least 500 consecutive nucleotides of SEQ ID NO: 1, and
   a sequence which is capable of hybridizing under medium stringency conditions with the nucleic acid sequence of SEQ ID NO:1 or its complementary strand.

Preferably, the isolated nucleic acid has a promoter activity specific of retinal ganglion cells.

Preferably, the nucleic acid of the invention has a length of less than 1.5 kb and comprises, or consists of, a sequence selected from the group consisting of the sequence of SEQ ID NO: 1, and a functional variant thereof having at least 80% identity to SEQ ID NO: 1. In particular, the nucleic acid of the invention may comprise, or consist of, a sequence having at least 80% or 90% identity to SEQ ID NO:1, or may comprise, or consist of, the sequence of SEQ ID NO:1.

Preferably, the nucleic acid of the invention has a length of less than 1.2 kb, more preferably of less than 1 kb.

In a second aspect, the present invention relates to an expression cassette comprising a nucleic acid of the invention operably linked to a nucleic acid encoding a polypeptide or nucleic acid of interest, preferably a polypeptide of interest.

In particular, the polypeptide of interest may be a therapeutic protein, an optogenetic actuator or a reporter protein. Preferably, the polypeptide of interest is a therapeutic protein or an optogenetic actuator.

In particular, the therapeutic protein may be selected from the group consisting of MT-ND4, MT-ND1, MT-ND6, MT-CYB, MT-CO3, MT-ND5, MT-ND2, MT-COI, MT-ATP6, MT-ND4L, OPA1, OPA3, OPA7 and ACO2, or may be a neurotrophic factor preferably selected from the group consisting of GDNF, VEGF, CNTF, FGF2, BDNF and EPO, an anti-apoptotic protein preferably selected from the group consisting of BCL2 and BCL2L1, an anti-angiogenic factor preferably selected from the group consisting of endostatin, angiostatin and sFlt, an anti-inflammatory factor preferably selected from the group consisting of IL10, IL1R1, TGFBI and IL4, or the rod-derived cone viability factor (RdCVF).

The optogenetic actuator may be an optogenetic activator, preferably selected from the group consisting of rhodopsins, photopsins, melanopsins, pinopsins, parapinopsins, VA opsins, peropsins, neuropsins, encephalopsins, retinochromes, RGR opsins, microbial opsins with red-shifted spectral properties such as ReaChR, Chrimson or ChrimsonR, vertebrate opsins that can recruit $G_{i/o}$ signalling such as short wavelength vertebrate opsin or long wavelength vertebrate opsin, channelrhodopsins from microalgae of the genus *Chlamydomonas* such as channelrhodopsin-1 and channelrhodopsin-2 (from *Chlamydomonas reinhardtii*), and variants thereof, or an optogenetic inhibitor, preferably selected from the group consisting of halorhodopsins such as halorhodopsin (NpHR), enhanced halorhodopsins (eNpHR2.0 and eNpHR3.0) and the red-shifted halorhodopsin Halo57, archaerhodopsin-3 (AR-3), archaerhodopsin (Arch), bacteriorhodopsins such as enhanced bacteriorhodopsin (eBR), proteorhodopsins, xanthorhodopsins, *Leptosphaeria maculans* fungal opsins (Mac), the cruxhalorhodopsin Jaws, and variants thereof.

The polypeptide of interest may also be a reporter protein, preferably selected from the group consisting of fluorescent proteins, calcium indicators, alkaline phosphatases, beta-galactosidases, beta-lactamases, horseradish peroxidase, and variants thereof.

In preferred embodiments, the polypeptide of interest is not SNCG protein and/or is not luciferase.

Alternatively, the nucleic acid of the invention may be operably linked to a nucleic acid encoding a nucleic acid of interest, preferably selected from the group consisting of an siRNA, an shRNA an RNAi, an miRNA, an antisense RNA, a ribozyme and a DNAzyme.

In a third aspect, the present invention relates to a vector comprising an expression cassette of the invention, preferably a viral vector, and more preferably a retroviral vector, in particular a lentiviral vector or a non-pathogenic parvovirus. The vector may be an adeno-associated viral (AAV) vector and may comprise two ITRs flanking the nucleic acid encoding the polypeptide or nucleic acid of interest.

In another aspect, the present invention relates to a viral particle comprising a vector of the invention. In particular an AAV particle comprising said vector and an AAV-derived capsid, preferably selected from the group consisting of AAV-2, AAV-5, AAV-7m8 (AAV2-7m8), AAV-9 and AAV-8 serotype capsid, more preferably AAV-2 derived capsid such as AAV-2 or AAV2-7m8 capsid.

In a further aspect, the invention also relates to a cell, preferably a retinal ganglion cell, transformed with an expression cassette, a vector or a viral particle of the invention.

In a further aspect, the invention also relates to a pharmaceutical composition comprising a nucleic acid, expression cassette, vector, viral particle or cell of the invention, and a pharmaceutically acceptable excipient.

In another aspect, the present invention relates to an expression cassette, a vector, a viral particle, or a cell of the invention, for use in the treatment of an ocular disease.

Preferably, the ocular disease is selected from diseases associated with retinal ganglion cell degeneration, more preferably selected from a hereditary optic neuropathy such as Leber's hereditary optic neuropathy or dominant optic atrophy, and diseases associated with photoreceptor cell degeneration such as age-related macular degeneration, cone-rod dystrophy, Leber congenital amaurosis, Stargardt's disease, diabetic retinopathy, retinal detachment, Best's disease, retinitis pigmentosa, choroideremia or a tapetoretinal degeneration.

In a further aspect, the present invention also relates to the use of a nucleic acid, expression cassette, vector or viral particle of the invention for the expression of a nucleic acid encoding a polypeptide or nucleic acid of interest in retinal ganglion cells, preferably for specific expression in retinal ganglion cells. It also relates to a method of expressing a polypeptide or nucleic acid of interest in retinal ganglion cells, preferably expressing a polypeptide or nucleic acid of interest specifically in retinal ganglion cells, comprising introducing a nucleic acid, expression cassette, vector or viral particle of the invention in retinal ganglion cells.

DETAILED DESCRIPTION OF THE INVENTION

Figure 1:
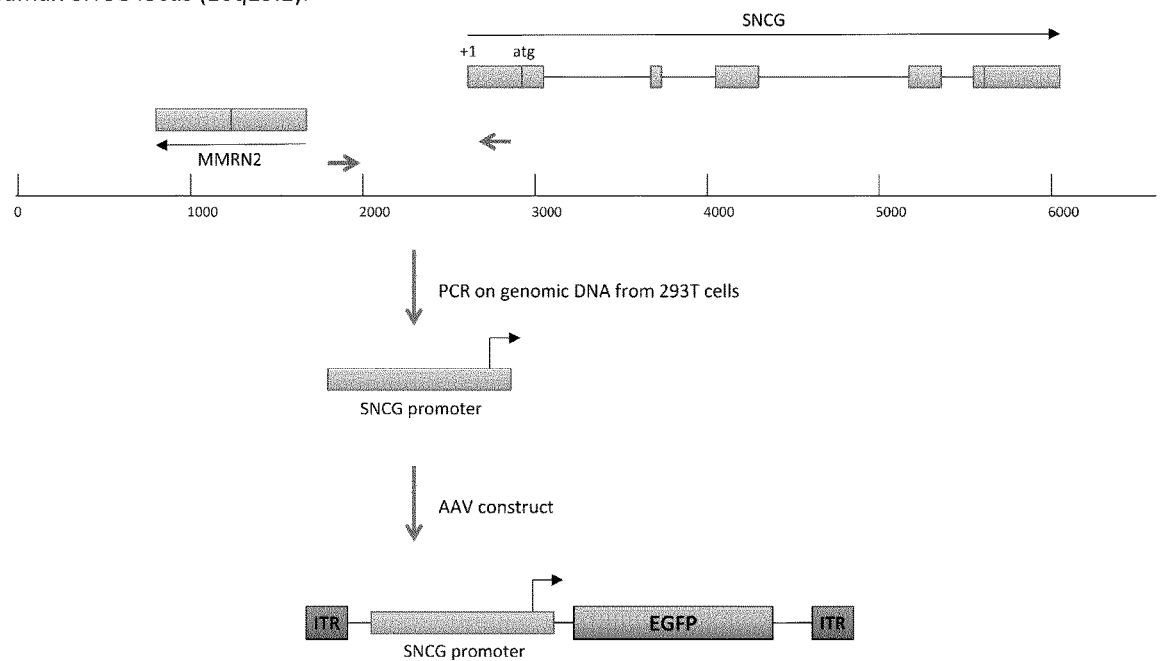
FIG. 1. Schematic representation of the SNCG gene and promoter sequence. The SNCG gene is located on chromosome 10 (10q23.3). It contains 5 exons extending over 3.5 kb from +1 transcription site to the end of the 5th exon. The 1st exon of the multimerine 2 gene (MMRN2) is located 863 bp downstream of +1 SNCG transcription site. In order to extract the human sequence of the SNCG promoter, the −785 to +163 region (indicated by arrows) was amplified from HEK 293T cells. The PCR product was then subcloned into pENTR-D/TOPO and sequenced. The sequence was identical to the Genebank sequence with GeneID6623. AAV vectors expressing the eGFP reporter gene under the control of the SNCG promoter sequence (SEQ ID NO: 1) were then produced.

The inventors herein identified a promoter sequence derived from the regulatory region of the human gamma-synuclein gene. This promoter has a length of less than 1 kb and can drive high-level gene expression specifically in retinal ganglion cells (RGCs). Thanks to its short length, this promoter can be easily used in AAV-mediated gene delivery and is particularly suitable to deliver long genes. The inventors demonstrated that this promoter, in combination with an AAV capsid, leads to strong and specific transgene expression in RGCs both in mice and non-human primates. Indeed, at the same AAV dose, this promoter provided a stronger transgene expression in RGCs than the ubiquitous CMV promoter. Furthermore, the inventors showed that, in primates, this promoter was also stronger than the CMV promoter.

Definitions

As used herein, the term "nucleic acid" or "polynucleotide" refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—$NH_2$) or a mixed phosphoramidate-phosphodiester oligomer. The nucleic acid of the invention can be prepared by any method known to one skilled in the art, including chemical synthesis, recombination, and mutagenesis. In preferred embodiments, the nucleic acid of the invention is a DNA molecule, preferably synthesized by recombinant methods well known to those skilled in the art.

As used herein, the term "isolated nucleic acid" refers to a nucleic acid molecule which has been identified and separated and/or recovered from a component of its natural environment. In particular, this term refers to a nucleic acid molecule which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

As used herein, the term "promoter" refers to a regulatory element that directs the transcription of a nucleic acid to which it is operably linked. A promoter can regulate both rate and efficiency of transcription of an operably linked nucleic acid. A promoter may also be operably linked to other regulatory elements which enhance ("enhancers") or repress ("repressors") promoter-dependent transcription of a nucleic acid.

As used herein, the term "promoter activity" refers to the ability of a promoter to initiate transcription of a nucleic acid to which it is operably linked. Promoter activity can be measured using procedures known in the art or as described in the Examples. For example, promoter activity can be measured as an amount of mRNA transcribed by using, for example, Northern blotting or polymerase chain reaction (PCR). Alternatively, promoter activity can be measured as an amount of translated protein product, for example, by Western blotting, ELISA, colorimetric assays and various activity assays, including reporter gene assays and other procedures known in the art or as described in the Examples.

The term "operably linked" refers, as used herein, to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" may refer to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "retinal ganglion cells" or "RGCs" refers to neurons of the innermost layer of the retina excluding the displaced amacrine cells. They integrate information from photoreceptors, via the bipolar cells of the retina, and project into the brain, where they synapse at the thalamus, the hypothalamus and the superior colliculus. The neural transcription factor BRN3A (Gene ID: 5457) was found to be specifically expressed in RGCs and antibodies against this protein are considered a reliable marker to identify and quantify RGCs (Quina et al. J. Neurosci. 2005; 25(50):11595-11604). Thus, in particular embodiments, the term "retinal ganglion cells" or "RGCs" refers to neurons of the innermost layer of the retina expressing BRN3A.

As used herein, the term "sequence identity" or "identity" refers to the number (%) of matches (identical nucleic acid residues) in positions from an alignment of two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005). Alignment for purposes of determining percent nucleic acid sequence identity can be achieved in various ways that are within the skill in the art, for instance, using publicly available computer software available on internet web sites such as Worldwide Website: blast.ncbi.nlm.nih.gov/ or ebi.ac.uk/Tools/emboss/. Those skilled in the art can determine appropriate parameters for measuring alignment, including any algorithms needed to achieve maximal alignment over the full length of the sequences being compared. For purposes herein, % nucleic acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The term "subject" or "patient" refers to an animal having retina, preferably to a mammal, even more preferably to a human, including adult, child and human at the prenatal stage.

In a first aspect, the present invention relates to a nucleic acid, preferably an isolated nucleic acid, having a promoter activity in retinal ganglion cells, having a length of less 2 kb and comprising, or consisting of, a sequence selected from the group consisting of the sequence of SEQ ID NO: 1 and functional variants thereof.

The nucleotide sequence of SEQ ID NO: 1 was derived from the regulatory region of the human gamma-synuclein gene (Symbol: SNCG; Gene ID: 6623). This gene encodes a member of the synuclein family of proteins which are believed to be involved in the pathogenesis of neurodegenerative diseases. It was further found that mutations in said gene are associated with breast tumor development. The gene is located on chromosome 10 (10q23.2-q23.3) (Genebank accession number NC_000010.11 from position 86958531 to position 86963260). As illustrated in FIG. 1, the promoter of SEQ ID NO: 1 comprises 953 nucleotides of the 5' regulatory region of the SNCG gene (from position −789 to position +164, the start codon of the protein being at position +168).

The nucleic acid of the invention exhibits a promoter activity in RGCs, i.e. when introduced in RGCs, it can initiate transcription of a nucleic acid to which it is operably linked. Preferably, the promoter activity is specific of RGCs. The term "specific of RGCs" shall be understood to mean a promoter mainly active in retinal ganglion cells. It shall be understood that a residual expression, generally lower, in other tissues or cells cannot be entirely excluded. In preferred embodiments, the promoter of the invention is not active in bipolar, amacrine, horizontal, Muller or cells or in photoreceptors.

In an embodiment, the promoter of the invention comprises, or consists of, the sequence of SEQ ID NO: 1.

In another embodiment, the promoter of the invention comprises, or consists of, a functional variant of SEQ ID NO: 1.

As used herein, the term "variant" refers to a nucleotide sequence differing from the original sequence, but retaining essential properties thereof. Generally, variants are overall closely similar, and, in many regions, identical to the original polynucleotide. The sequence of the variant may differ by nucleotide substitutions, deletions or insertions of one or more nucleotides in the sequence, which do not impair the promoter activity. The variant may have the same length of the original sequence, or may be shorter or longer.

The term "functional variant" refers to a variant of SEQ ID NO: 1 that exhibits a promoter activity of SEQ ID NO: 1, i.e. that exhibits a promoter activity in RGC, preferably a promoter activity specific of RGCs.

In an embodiment, the promoter of the invention comprises, or consists of, a functional variant of SEQ ID NO: 1 selected from the group consisting of
- a sequence having at least 80% identity to SEQ ID NO:1,
- a sequence comprising at least 100 consecutive nucleotides of SEQ ID NO: 1, and
- a sequence which is capable of hybridizing under low, medium or high stringency conditions with the nucleic acid sequence of SEQ ID NO:1 or its complementary strand.

In a particular embodiment, the promoter of the invention comprises, or consists of, a functional variant having at least 80, 81, 82, 83, 84, 85, 86, 87, 88, 89, 90, 91, 92, 93, 94, 95, 96, 97, 98 or 99% identity to SEQ ID NO: 1, preferably over the entire sequence of SEQ ID NO: 1. The promoter of the invention may differ from the polynucleotide of SEQ ID NO: 1 by 1, 2, 3, 4, 5, 6, 7, 8, 9, 10, 11, 12, 13, 14 or 15 substitutions, deletions and/or insertions.

In another particular embodiment, the promoter of the invention comprises, or consists of, a functional variant having a sequence comprising at least 100, 200, 300, 400, 500, 600, 700, 800, 900 consecutive nucleotides of SEQ ID NO: 1. Preferably, it comprises, or consists of, a functional variant having a sequence comprising at least 500 consecutive nucleotides of SEQ ID NO: 1.

In a further particular embodiment, the promoter of the invention comprises, or consists of, a functional variant having a sequence capable of hybridizing under low, medium or high stringency conditions with the nucleic acid sequence of SEQ ID NO: 1 or its complementary strand, preferably under medium stringency conditions, more preferably under high stringency conditions.

As used herein, the term "low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/mL sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

One of the main advantage of the promoter sequence of the invention is its small size. Indeed, the promoter of the invention has a length of less 2 kb and is thus particularly suitable for use in AAV vectors wherein the DNA payload is severely limited.

In preferred embodiments, the length of the promoter of the invention is of less than 1.5 kb, preferably of less than 1.4, 1.3, 1.2, 1.1 or 1 kb, more preferably of less than 990, 980, 970 or 960 bases.

In some embodiments, the promoter of the invention is not operably linked to SNCG gene, and in particular to the human SNCG gene. In some other embodiments, the promoter of the invention is not operably linked to a gene encoding a reporter protein, and in particular to a gene encoding luciferase. Preferably, the promoter of the invention is not operably linked to SNCG gene or to a gene encoding luciferase.

In a second aspect, the present invention relates to an expression cassette comprising a promoter of the invention operably linked to a nucleic acid of interest.

The nucleic acid operably linked to the promoter of the invention may encode a polypeptide of interest or a nucleic acid of interest.

As used herein, the term "expression cassette" refers to a nucleic acid construct comprising a coding sequence and one or more control sequences required for expression of said coding sequence. In particular, one of these control sequence is a promoter of the invention. Generally, the expression cassette comprises a coding sequence and regulatory sequences preceding (5' non-coding sequences) and following (3' non-coding sequences) the coding sequence that are required for expression of the selected gene product. Thus, an expression cassette typically comprises a promoter sequence, a coding sequence and a 3' untranslated region that usually contains a polyadenylation site and/or transcription terminator. The expression cassette may also comprise additional regulatory elements such as, for example, enhancer sequences, a polylinker sequence facilitating the insertion of a DNA fragment within a vector and/or splicing signal sequences. The expression cassette is usually included within a vector, to facilitate cloning and transformation.

Preferably, the promoter of the invention is operably linked to a heterologous nucleic acid. As used herein, the term "heterologous" means a nucleic acid other than the nucleic acid that the promoter is operably linked to in a naturally occurring genome. In particular, in some embodiments, the promoter of the invention is not operably linked to SNCG gene, and in particular to the human SNCG gene. In some other embodiments, the promoter of the invention is not operably linked to a gene encoding luciferase. Preferably, the promoter of the invention is neither operably linked to SNCG gene nor to a gene encoding luciferase.

In an embodiment, the nucleic acid operably linked to the promoter of the invention encodes a polypeptide of interest.

The polypeptide of interest may be any polypeptide of which expression in RGCs is desired. In particular, the polypeptide of interest may be a therapeutic polypeptide, reporter protein or optogenetic actuator.

In an embodiment, the nucleic acid operably linked to the promoter of the invention is a therapeutic gene, i.e. encodes a therapeutic polypeptide.

As used herein, the term "therapeutic gene" refers to a gene encoding a therapeutic protein which is useful in the treatment of a pathological condition. The therapeutic gene, when expressed, confers a beneficial effect on the cell or tissue in which it is present, or on a patient in which the gene is expressed. Examples of beneficial effects include amelioration of a sign or symptom of a condition or disease, prevention or inhibition of a condition or disease, or conferral of a desired characteristic. Therapeutic genes include genes that partially or wholly correct a genetic deficiency in the patient. In particular, the therapeutic gene may be, without limitation, a nucleic acid sequence encoding a protein useful in gene therapy to relieve deficiencies caused by missing, defective or sub-optimal levels of said protein in a cell or tissue of a subject. The therapeutic polypeptide may, e.g., supply a polypeptide and/or enzymatic activity that is absent, defective or present at a sub-optimal level in RGCs, supply a polypeptide and/or enzymatic activity that indirectly counteracts an imbalance in RGCs. The therapeutic polypeptide may also be used to reduce the activity of a polypeptide by acting, e.g., as a dominant-negative polypeptide. Preferably, the therapeutic polypeptide supplies a polypeptide and/or enzymatic activity that is absent, defective or present at a sub-optimal level in RGCs, more preferably a polypeptide and/or enzymatic activity that is absent or defective in RGCs.

Examples of therapeutic genes include, but are not limited to, nucleic acids for replacement of a missing or mutated gene known to cause retinal disease such as MT-ND4 (Gene ID: 4538), MT-ND1 (Gene ID: 4535), MT-ND6 (Gene ID: 4541), MT-CYB (Gene ID: 4519), MT-CO3 (Gene ID: 4514), MT-ND5 (Gene ID: 4540), MT-ND2 (Gene ID: 4536), MT-COI (Gene ID: 4512), MT-ATP6 (Gene ID: 4508), MT-ND4L (Gene ID: 4539), OPA1 (Gene ID: 4976), OPA3 (Gene ID: 80207), OPA7 (Gene ID: 84233), ACO2 and (Gene ID: 50).

The therapeutic gene may also encode neurotrophic factors such as GDNF (Gene ID: 2668), CNTF (Gene ID: 1270), FGF2 (Gene ID: 2247), BDNF (Gene ID: 627) and EPO (Gene ID: 2056), anti-apoptotic genes such as BCL2 (Gene ID: 596) and BCL2L1 (Gene ID: 598), anti-angiogenic factors such as endostatin, angiostatin and sFlt, anti-inflammatory factors such as IL10 (Gene ID: 3586), IL1R1 (Gene ID: 3554), TGFBI (Gene ID; 7045) and IL4 (Gene ID: 3565), or the rod-derived cone viability factor (RdCVF) (Gene ID: 115861).

Preferably, the therapeutic gene is selected from the group consisting of MT-ND4 (Gene ID: 4538), MT-ND1 (Gene ID: 4535), MT-ND6 (Gene ID: 4541), MT-CYB (Gene ID: 4519), MT-CO3 (Gene ID: 4514), MT-ND5 (Gene ID: 4540), MT-ND2 (Gene ID: 4536), MT-COI (Gene ID: 4512), MT-ATP6 (Gene ID: 4508) and MT-ND4L (Gene ID: 4539). More preferably, the therapeutic gene is selected from the group consisting of MT-ND4 (Gene ID: 4538), MT-ND1 (Gene ID: 4535) and MT-ND6 (Gene ID: 4541).

Additional signal peptide may be added to therapeutic proteins, in particular in order to import them inside certain organelles (such as mitochondria), to secrete them from the cell, or to insert them into cellular membrane.

In another embodiment, the polypeptide of interest is an optogenetic actuator.

As used herein, the term "optogenetic actuator" refers to a photochemically reactive polypeptide that uses vitamin A or isoforms thereof as its chromophore. An optogenetic actuator is a light-gated ion pump or channel that absorbs light and is activated by light. The optogenetic actuator may be from a prokaryotic organism or a eukaryotic organism. In particular, it may be a microbial opsin or a vertebrate opsin. The optogenetic actuator may be an optogenetic activator or an optogenetic inhibitor.

An optogenetic activator causes a cell to depolarize upon exposure to light. When a cell depolarizes, the negative internal charge of the cell becomes positive for a brief period. The shift from a negative to a positive internal cellular environment allows the transmission of electrical impulses both within a cell and, optionally, between cells. Examples of optogenetic activators include, but are not limited to, rhodopsins, photopsins, melanopsins, pinopsins, parapinopsins, VA opsins, peropsins, neuropsins, encephalopsins, retinochromes, RGR opsins, microbial opsins with red-shifted spectral properties such as ReaChR, Chrimson or ChrimsonR, vertebrate opsins that can recruit $G_{i/o}$ signalling such as short wavelength vertebrate opsin or long wavelength vertebrate opsin, channelrhodopsins from microalgae of the genus *Chlamydomonas* such as channelrhodopsin-1, channelrhodopsin-2 (from *Chlamydomonas reinhardtii*), and variants, thereof. Numerous variants (e.g. codon optimized variants, mutants, chimeras) of channelrhodopsin are being generated to improve certain features of these proteins. Examples of these variants include, but are not limited to, hChR2 (L132C), ChR2 (H134R), ChETA (E123T), C1V1 (E122T), C1V1 (E162T), C1V1 (E122/162T), hChR2 (C128A), hChR2 (C128S), hChR2 (C128T), hChR2 (C128A/H134R), hCatch (T159S), hChief, hChR2 (C128S/D156A), hChR2 (T159C), hChR2 (E123T/T159C), hChR2c (C128T), ChR2c (C128T), ChR2e (Q117C) and SwitChR (for review see Prakash et al. Nat Methods. 2012 December; 9(12):1171-9).

An optogenetic inhibitor causes a cell to hyperpolarize upon exposure to light. When a cell hyperpolarizes, the negative internal charge of the cell becomes more negative for a brief period. The shift to more negative inhibits action potentials by increasing the stimulus required to move the membrane potential to the action potential threshold. In a specific embodiment, an optogenetic inhibitor is a light-gated ion pump that upon absorption of a photon transports chloride ions inward and/or transports cations outward. Any suitable light-gated, retinal-dependent, ion pump that transports chloride ions inward or cations outward upon absorption of a photon may be used as an optogenetic inhibitor.

Examples of optogenetic inhibitors include, but are not limited to, halorhodopsins such as halorhodopsin (NpHR), enhanced halorhodopsins (eNpHR2.0 and eNpHR3.0) and the red-shifted halorhodopsin Halo57, archaerhodopsin-3 (AR-3), archaerhodopsin (Arch), bacteriorhodopsins such as enhanced bacteriorhodopsin (eBR), proteorhodopsins, xanthorhodopsins, *Leptosphaeria maculans* fungal opsins (Mac), the cruxhalorhodopsin Jaws, and variants thereof.

In a more particularly preferred embodiment, the optogenetic actuator is an optogenetic activator, preferably selected from channelrhodopsins, ChrimsonR and variants thereof, and more preferably selected from hChR2 (L132C)-hCatCh and ChrimsonR-tdTomato.

In a more particularly preferred embodiment, the optogenetic actuator is an optogenetic activator, preferably selected from channelrhodopsins and variants thereof, and more preferably is hChR2 (L132C)-hCatCh.

In a further embodiment, the nucleic acid operably linked to the promoter of the invention encodes a reporter protein. Preferably, the reporter protein is detectable in living RGCs. The expression of a reporter protein under the control of a promoter of the invention allows specifically detecting or identifying RGCs. The reporter protein may be, for example, a fluorescent protein (e.g., GFP), calcium indicator (e.g. GCaMP), luciferase, alkaline phosphatase, beta-galactosidase, beta-lactamase, horseradish peroxidase, and variants thereof. In a particular embodiment, the reporter protein is selected from the group consisting of fluorescent proteins, calcium indicators, alkaline phosphatases, beta-galactosidases, beta-lactamases, horseradish peroxidase, and variants thereof.

In another embodiment, the nucleic acid operably linked to the promoter of the invention encodes a nucleic acid of interest.

The nucleic acid of interest may be any nucleic acid of which expression in RGCs is desired. In particular, the nucleic acid of interest may be a therapeutic nucleic acid.

The nucleic acid may be, for example, an siRNA, an shRNA an RNAi, an miRNA, an antisense RNA, a ribozyme or a DNAzyme.

In a particular embodiment, the nucleic acid encodes an RNA that when transcribed from the nucleic acid operably linked to the promoter of the invention can treat or prevent an ocular disease by interfering with translation or transcription of an abnormal or excess protein associated with said disorder. For example, the nucleic acid of interest may encode for an RNA, which treats the disease by highly specific elimination or reduction of mRNA encoding the abnormal and/or excess proteins.

The expression cassette of the invention may comprise one or more nucleic acids operably linked to the promoter of the invention. For example, the promoter may be operably linked to one or more therapeutic genes and a nucleic acid encoding a reporter protein or to a therapeutic gene and an optogenetic actuator.

All the embodiments of promoter of the invention are also contemplated in this aspect.

In a third aspect, the present invention relates to a vector comprising the promoter of the invention or the expression cassette of the invention.

As used herein, the term "vector" refers to a nucleic acid molecule used as a vehicle to transfer genetic material, and in particular to deliver a nucleic acid into a host cell, either in vitro or in vivo. Vectors include, but are not limited to, plasmids, phasmids, cosmids, transposable elements, viruses, and artificial chromosomes (e.g., YACs).

Preferably, the vector of the invention is a vector suitable for use in gene or cell therapy, and in particular is suitable to target RGCs.

The vector of the invention is preferably a viral genome vector including any element required to establish the expression of the polypeptide of interest in a host cell such as, for example, a promoter, e.g., a promoter of the invention, an ITR, a ribosome binding element, terminator, enhancer, selection marker, intron, polyA signal, and/or origin of replication.

In some embodiments, the vector is a viral vector, such as vectors derived from Moloney murine leukemia virus vectors (MoMLV), MSCV, SFFV, MPSV or SNV, lentiviral vectors (e.g. derived from human immunodeficiency virus (HIV), simian immunodeficiency virus (SIV), feline immunodeficiency virus (FIV), bovine immunodeficiency virus (BIV) or equine infectious anemia virus (EIAV)), adenoviral (Ad) vectors, adeno-associated viral (AAV) vectors, simian virus 40 (SV-40) vectors, bovine papilloma virus vectors, Epstein-Ban virus, herpes virus vectors, vaccinia virus vectors, Harvey murine sarcoma virus vectors, murine mammary tumor virus vectors, Rous sarcoma virus vectors.

In particular embodiments, the vector is a retroviral vector, preferably a lentiviral vector or a non-pathogenic parvovirus.

As is known in the art, depending on the specific viral vector considered for use, suitable sequences should be introduced in the vector of the invention for obtaining a functional viral vector, such as AAV ITRs for an AAV vector, or LTRs for lentiviral vectors.

In preferred embodiments, the vector is an AAV vector.

The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter). Therefore AAV has arisen considerable interest as a potential vector for human gene therapy. Among the favorable properties of the virus are its lack of association with any human disease, its ability to infect both dividing and non-dividing cells, and the wide range of cell lines derived from different tissues that can be infected.

As used herein, the term "AAV vector" refers to a polynucleotide vector comprising one or more heterologous sequences (i.e., nucleic acid sequence not of AAV origin) that are flanked by at least one AAV inverted terminal repeat sequence (ITR), preferably two ITRs. Such AAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins).

An "inverted terminal repeat" or "ITR" sequence is a term well understood in the art and refers to relatively short sequences found at the termini of viral genomes which are in opposite orientation. An "AAV inverted terminal repeat (ITR)" sequence is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C and D regions), allowing intra-strand base-pairing to occur within this portion of the ITR. AAV ITRs for use in the vectors of the invention may have a wild-type nucleotide sequence or may be altered by the insertion, deletion or substitution. The serotype of the inverted terminal repeats (ITRs) of the AAV vector may be selected from any known human or nonhuman AAV serotype.

When an AAV vector is incorporated into a larger polynucleotide (e.g., in a chromosome or in another vector such as a plasmid used for cloning or transfection), then the AAV vector may be referred to as a "pro-vector" which can be "rescued" by replication and encapsidation in the presence of AAV packaging functions and suitable helper functions. The AAV vector of the invention can be in any of a number of forms, including, but not limited to, plasmids, linear artificial chromosomes, complexed with lipids, encapsulated within liposomes, and encapsidated in a viral particle, e.g., an AAV particle.

The promoter or expression cassette of the invention may be introduced into the vector by any method known by the skilled person.

The vector may further comprise one or more nucleic acid sequences encoding selectable marker such as auxotrophic markers (e.g., LEU2, URA3, TRP 1 or HIS3), detectable labels such as fluorescent or luminescent proteins (e.g., GFP, eGFP, DsRed, CFP), or protein conferring resistance to a chemical/toxic compound (e.g., MGMT gene conferring resistance to temozolomide). These markers can be used to select or detect host cells comprising the vector and can be easily chosen by the skilled person according to the host cell.

All the embodiments of promoter and expression cassette of the invention are also contemplated in this aspect.

The vector of the invention may be packaged into a virus capsid to generate a "viral particle". Thus, in a further aspect, the present invention also relates to a viral particle comprising a vector of the invention.

In a particular embodiment, the vector is an AAV vector and is packaged into an AAV-derived capsid to generate an "adeno-associated viral particle" or "AAV particle". Thus, used herein, the term "AAV particle" refers to a viral particle composed of at least one AAV capsid protein and an encapsidated AAV vector genome.

The capsid serotype determines the tropism range of the AAV particle.

Multiple serotypes of adeno-associated virus (AAV), including 12 human serotypes and more than 100 serotypes from nonhuman primates have now been identified (Howarth al., 2010, Cell Biol Toxicol 26: 1-10). Among these serotypes, human serotype 2 was the first AAV developed as a gene transfer vector. Other currently used AAV serotypes include, but are not limited to, AAV1, AAV3, AAV4, AAV5, AAV6, AAV7, AAV8, AAVrh8, AAV9, AAV10, AAVrh10, AAV11, AAV12, AAVrh74 and AAVdj, etc. In addition, non-natural engineered variants and chimeric AAV can also be useful. In particular, the capsid proteins may be variants comprising one or more amino acid substitutions enhancing transduction efficiency.

Different AAV serotypes are used to optimize transduction of particular target cells or to target specific cell types within a particular target tissue (e.g., RGCs). An AAV particle can comprise viral proteins and viral nucleic acids of the same serotype or any natural or artificial sequence variant of AAV. For example, the AAV particle may comprise AAV2 capsid proteins and at least one, preferably two, AAV2 ITR. Any combination of AAV serotypes for production of an AAV particle is provided herein as if each combination had been expressly stated herein.

In preferred embodiment, the AAV particle comprises an AAV-derived capsid selected from the group consisting of AAV2, AAV-5, AAV-7m8 (AAV2-7m8, Dalkara et al. Sci Transl Med (2013), 5, 189ra76), AAV9 or AAV8 capsid.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a VP1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid or a mutated AAV capsid.

A chimeric capsid comprises VP capsid proteins derived from at least two different AAV serotypes or comprises at least one chimeric VP protein combining VP protein regions or domains derived from at least two AAV serotypes.

Capsid proteins may also be mutated, in particular to enhance transduction efficiency. Mutated AAV capsids may be obtained from capsid modifications inserted by error prone PCR and/or peptide insertion or by including one or several amino acids substitutions. In particular, mutations may be made in any one or more of tyrosine residues of natural or non-natural capsid proteins (e.g. VP1, VP2, or VP3). Preferably, mutated residues are surface exposed tyrosine residues. Exemplary mutations include, but are not limited to tyrosine-to-phenylalanine substitutions such as Y252F, Y272F, Y444F, Y500F, Y700F, Y704F, Y730F, Y275F, Y281F, Y508F, Y576F, Y612G, Y673F and Y720F.

In a preferred embodiment, the AAV particle comprise an AAV2-derived capsid. In this embodiment, the capsid may comprise one or more tyrosine-to-phenylalanine substitutions, preferably comprises Y444F substitution.

In addition, the genome vector (i.e. a vector of the invention) of the AAV particle may either be a single stranded or self-complementary double-stranded genome. Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers. In a preferred embodiment, the AAV particle implemented in the practice of the present invention has a single stranded genome.

Numerous methods are known in the art for production of viral particles, and in particular AAV particles, including transfection, stable cell line production, and infectious hybrid virus production systems which include adenovirus-AAV hybrids, herpesvirus-AAV hybrids (Conway, J E et al., (1997) Virology 71(11):8780-8789) and baculovirus-AAV hybrids).

AAV production cultures for the production of AAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a nucleic acid of interest flanked by at least one AAV ITR sequences, e.g., a vector of the invention; and 5) suitable media and media components to support AAV production that are well-known in the art.

In practicing the invention, host cells for producing AAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV particles are then purified and formulated using standard techniques known in the art.

All the embodiments of promoter, expression cassette and vector of the invention are also contemplated in this aspect.

In another aspect, the present invention also relates to an isolated host cell transformed or transfected with an expression cassette, vector or viral particle of the invention.

The host cell may be any animal cell, plant cell, bacterium cell or yeast. Preferably, the host cell is a mammalian cell or an insect cell. More preferably, the host cell is a human cell.

In preferred embodiments, the host cell is a retinal ganglion cell, in particular a human RGC.

The expression cassette or vector of the invention may be transferred into host cells using any known technique including, but being not limited to, calcium phosphate-DNA precipitation, DEAE-Dextran transfection, electroporation, microinjection, biolistic, lipofection, or viral infection, and may be maintained in the host cell in an ectopic form or may be integrated into the genome.

In preferred embodiments, the expression cassette or vector of the invention is transferred into the host cell by viral infection, preferably using a viral particle of the invention, more preferably using an AAV particle of the invention.

All the embodiments of promoter, expression cassette, vector and viral particle of the invention are also contemplated in this aspect.

The present invention also relates to a pharmaceutical composition comprising an expression cassette, vector, viral particle or cell of the invention.

Such compositions comprise a therapeutically effective amount of the therapeutic agent (an expression cassette, vector, viral particle or cell of the invention), and a pharmaceutically acceptable excipient. As used herein, the term "pharmaceutically acceptable" means approved by a regulatory agency or recognized pharmacopeia such as European Pharmacopeia, for use in animals and/or humans. The term "excipient" refers to a diluent, adjuvant, carrier, or vehicle with which the therapeutic agent is administered.

As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolality, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various tween compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences, 15th Edition.

Preferably, the composition is formulated to be administered to the eye, in particular by intraocular injection, e.g., by subretinal and/or intravitreal administration. Accordingly, the composition can be combined with pharmaceutically acceptable excipient such as saline, Ringer's balanced salt solution (pH 7.4), and the like.

The pharmaceutical compositions described herein can be packaged in single unit dosages or in multidosage forms.

In an embodiment, the pharmaceutical composition comprises a vector or viral particle of the invention, more preferably an AAV vector or particle.

In another embodiment, the pharmaceutical composition comprises host cells of the invention, preferably human host cell of the invention, i.e. transformed or transfected with an expression cassette, vector or viral particle of the invention, preferably with an AAV particle. Optionally, the composition comprising host cells may be frozen for storage at any temperature appropriate for storage of the cells. For example, the cells may be frozen at about −20° C., −80° C. or any other appropriate temperature. Cryogenically frozen cells may be stored in appropriate containers and prepared for storage to reduce risk of cell damage and maximize the likelihood that the cells will survive thawing. Alternatively, the cells may also be maintained at room temperature of refrigerated, e.g. at about 4° C.

The amount of pharmaceutical composition to be administered may be determined by standard procedure well known by those of ordinary skill in the art. Physiological data of the patient (e.g. age, size, and weight) and type and severity of the disease being treated have to be taken into account to determine the appropriate dosage.

The pharmaceutical composition of the invention may be administered as a single dose or in multiple doses.

In a particular embodiment, the composition comprises viral particles of the invention and each unit dosage comprises from $10^8$ to $10^{13}$ viral particles, preferably from $10^9$ to $10^{12}$ particles.

The pharmaceutical composition may further comprise one or several additional active compounds such as corticosteroids, antibiotics, analgesics, immunosuppressants, trophic factors, or any combinations thereof.

All the embodiments of promoter, expression cassette, vector, viral particle and host cell of the invention are also contemplated in this aspect.

In a further aspect, the present invention also relates to
a pharmaceutical composition of the invention for use in the treatment of an ocular disease,
an expression cassette, vector, viral particle or host cell of the invention for use in the treatment of an ocular disease,
the use of an expression cassette, vector, viral particle or host cell of the invention for the manufacture of a medicament for the treatment of an ocular disease, and
a method for treating an ocular disease comprising administering a therapeutically efficient amount of a pharmaceutical composition of the invention to a subject in need thereof.

In an embodiment, the ocular disease is a disease associated with retinal ganglion cell degeneration.

Examples of diseases associated with retinal ganglion cell degeneration include, but are not limited to, hereditary optic neuropathy (Leber's hereditary optic neuropathy, dominant optic neuropathy), compressive optic neuropathy (orbital pseudotumor, thyroid eye disease), autoimmune optic neuropathy (Lupus), diabetic retinopathy, glaucomatous optic nerve disease (GOND) including glaucoma, arteritic ischemic optic neuropathy (giant cell arteritis), nonarteritic ischemic optic neuropathy, infiltrative optic neuropathy (sarcoidosis), infectious optic neuropathy (syphilis, lyme, toxoplasmosis, herpes zoster), optic neuritis from demyelinating disease, posradiation optic neuropathy and acrodermatitis enteropathica.

In a particular embodiment, the ocular disease is a hereditary optic neuropathy, preferably selected from the group consisting of Leber's hereditary optic neuropathy (LHON; OMIM #535000), optic atrophy 1 (Kjer type optic atrophy; OMIM #165500), optic atrophy and cataract (optic atrophy 3; OMIM #165300), and optic atrophy 7 with or without auditory neuropathy (OMIM #612989).

Preferably, the ocular disease is a hereditary ocular disease associated with retinal ganglion cell degeneration, e.g. LHON or a dominant optic atrophy, and the polypeptide of interest expressed from the expression cassette, vector or viral particle of the invention is a therapeutic protein, in particular a therapeutic protein correcting the genetic deficiency in the patient.

In a preferred embodiment, the ocular disease is selected from the group consisting of LHON and a dominant optic atrophy, preferably selected from optic atrophy 1, optic atrophy and cataract (optic atrophy 3) and optic atrophy 7 with or without auditory neuropathy, and the polypeptide of interest is selected from the group consisting of MT-ND4, MT-ND1, MT-ND6, MT-CYB, MT-CO3, MT-ND5, MT-ND2, MT-COI, MT-ATP6, MT-ND4L, OPA1, OPA3, OPA7 and ACO2.

RGCs persist for extended periods after photoreceptor degeneration in diseases where photoreceptors are lost due to inherited or acquired disease. RGCs thus constitute targets for treatments to reanimate the retina using optogenetics. In this context, RGCs are the cellular targets independent of the degenerating cells where the expression of a photosensitive protein, i.e. an optogenetic actuator, in a strong and restricted manner is essential to the success of vision restoration.

Thus, in another embodiment, the ocular disease is a disease associated with photoreceptor cell degeneration. Preferably, in this embodiment, the polypeptide of interest is an optogenetic actuator as described above and the treatment is an optogenetic treatment.

Examples of diseases associated with photoreceptor cell degeneration, include but are not limited to, age-related macular degeneration, Leber's hereditary optic neuropathy, cone-rod dystrophy, Leber congenital amaurosis, Stargardt's disease, diabetic retinopathy, retinal detachment, Best's disease, retinitis pigmentosa, choroideremia and a tapetoretinal degeneration.

Alternatively, the ocular disease is selected from disease which are not necessarily or specifically associated with retinal ganglion cell or photoreceptor cell degeneration, but which can be treated or prevented by expressing specifically nucleic acid encoding a polypeptide or nucleic acid of interest in retinal ganglion cells (e.g. glaucoma).

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

In particular, the term "treatment of an ocular disease" may refer to a treatment to provide enhanced vision, to prevent progression of the disease to total blindness, to prevent spread of damage to uninjured ocular cells, to improve damage in injured ocular cells, to prevent the occurrence of retinal damage or to rescue eyes having mild or advanced disease. In some embodiments, this term refers to a treatment to prevent, reduce or stop RGCs degeneration by providing a therapeutic protein correcting a genetic deficiency of the patient. In some other embodiments, this term refers to a treatment to reanimate the retina or restore vision, using optogenetics.

By a "therapeutically efficient amount" is intended an amount of pharmaceutical composition of the invention administered to a subject that is sufficient to constitute a treatment as defined above of ocular disease.

The pharmaceutical composition may be administered as a single dose or in multiple doses.

In a particular embodiment, the pharmaceutical composition comprises viral particles of the invention and each unit dose comprises from $10^8$ to $10^{13}$ viral particles, preferably from $10^9$ to $10^{12}$ particles.

In the method for treating ocular disease of the invention, the pharmaceutical composition of the invention is preferably administered intraocularly, more preferably by subretinal or intravitreal administration.

The method of the invention may also further comprise administering at least one additional therapeutic agent to the subject. In particular, said therapeutic agent may be selected from the group consisting of a corticosteroid, an antibiotic, an analgesic, an immunosuppressant, or a trophic factor, or any combinations thereof.

The composition of the invention may be administered before or after the disease becomes symptomatic, e.g., before or after partial or complete RGC or photoreceptor cell degeneration and/or before or after partial or complete loss of vision.

All the embodiments of promoter, expression cassette, vector, viral particle, host cell and pharmaceutical composition of the invention are also contemplated in this aspect.

RGCs collectively transmit image-forming and non-image forming visual information from the retina in the form of action potential to the brain. There is thus a great interest in studying RGC function as the shape, size and projections of each type of RGC are distinctive and as they are thought to play quite different and possibly independent roles in visual function.

Thus, in another aspect, the present invention also relates to a non-human animal model comprising an expression cassette, vector, viral particle or host cell of the invention.

Such animal model may be used for in vivo studies of RGC functions. Using the promoter, cassette, vector or viral particle of the invention, it is possible to identify or track RGC, or monitor their activity, for example through expression of reporter proteins or voltage or calcium sensitive proteins.

The non-human animal model may also be used in screening methods for identifying or selecting pharmaceutical agent acting on RGCs.

Preferably, the non-human animal model is a mammal, more preferably a primate, rodent, rabbit or mini-pig.

The promoter, expression cassette or vector may be maintained in cells of this model in an episomic form or may be integrated into its genome.

Methods for transfecting or transforming animal cells or for producing transgenic animals expressing a nucleic acid sequence of interest under to control of a chosen promoter, i.e. the promoter of the invention, is well known by the skilled person and may be easily adapted according to cells and animals.

All the embodiments of promoter, expression cassette, vector, viral particle, host cell of the invention are also contemplated in this aspect.

All patents, patent applications, provisional applications, and publications referred to or cited herein are incorporated by reference in their entirety, including all figures and tables, to the extent they are not inconsistent with the explicit teachings of this specification.

The following examples are given for purposes of illustration and not by way of limitation.

EXAMPLES

Materials and Methods
Animals

All experiments were done in accordance with the National Institutes of Health Guide for Care and Use of Laboratory Animals. The protocol was approved by the Local Animal Ethics Committees and conducted in accordance with Directive 2010/63/EU of the European Parliament. All mice used in this study were C3H/HeN (rd1 mice) or C57Bl6J mice (wild type) from Janvier Laboratories (Le Genest Saint Isle, France) or cynomolgus macaques (*macaca fasicularis*) from foreign origin.

AAV Production

Recombinant AAVs were produced by the plasmid co-transfection method (Choi et al. Curr. Protoc. Hum. Genet. 2007; Chapter 12: Unit 12.9), and the resulting lysates were purified via iodixanol gradient ultracentrifugation as previously described. Briefly 40% iodixanol fraction was concentrated and buffer exchanged using Amicon Ultra-15 Centrifugal Filter Units. Vector stocks were then tittered for DNase-resistant vector genomes by real time PCR relative to a standard (Aurnhammer C et al. Hum Gene Ther Methods. 2012 February; 23(1):18-28).

Injections

Mice were anesthetized with ketamine (50 mg/kg) xylazine (10 mg/kg Rompum). Pupils were dilated and an ultrafine 30-gauge disposable needle was passed through the sclera, at the equator and next to the limbus, into the vitreous cavity. Injection of 1 µl stock containing $10^7$ to $10^{11}$ particles of AAV was made with direct observation of the needle in the center of the vitreous cavity. Primates were anesthetized with 10:1 mg/kg ketamine:xylazine. Pupils were dilated and 100 µL of viral vector containing either $1\times10^{11}$ or $5\times10^{11}$ viral particles were injected into the vitreous of each eye through the sclera approximately 4 mm behind the limbus, using a 30-gauge needle. Ophthalmic steroid and antibiotic ointment was applied to the corneas post-injection.

Immunohistochemistry

Transduced mouse retinas were dissected and fixed in 4% paraformaldehyde for 30 min at room temperature and washed with PBS. Retinas were then treated in PBS with 1% Triton X-100, 0.5% Tween 20 and 5% Bovine Serum Albumin blocking buffer for 1 h at room temperature (RT). Mice retinas were incubated overnight at 4° C. with polyclonal antibodies directed against GFP (Life Technologies; 1:2000) and monoclonal anti-Brn3a antibody (Millipore Chemicon; 1:100) in half diluted blocking buffer. Retinas were then incubated with secondary anti-rabbit IgG, anti-mouse IgG conjugated with Alexa TM594, Alexa TM488 and Alexa TM647 respectively (Molecular Probes; 1:500) for 1 h at RT, in half diluted blocking buffer. Primate retinas were labelled with antibodies directed against Brn3a, GFP and Channelrhodopsin in similar conditions. Cell nuclei were subsequently revealed by incubating the specimens with 4',6-diamidino-2-phenylindole (Sigma-Aldrich; 10 µg/mL). Retinas were rinsed and flat-mounted in mounting medium between two coverslips prior to initial confocal acquisition. Tissue sections of the previously labelled flat mounts were obtained by unmounting, cryopreserving and embedding in OCT before cryosections (15 µm) and observed by confocal microscopy.

Confocal Microscopy

Confocal microscopy was performed on an Olympus FV1000 laser-scanning confocal microscope. Images were acquired sequentially, line-by-line, in order to reduce excitation and emission crosstalk, step size was defined according to the Nyquist-Shannon sampling theorem. Exposure settings that minimized oversaturated pixels in the final images were used. Twelve bit Images were then processed with FIJI, Z-sections were projected on a single plane using maximum intensity under Z-project function and finally converted to 8-bit RGB colour mode.

Efficiency of transduction was assessed by counting Brn3a(+) cells transduced with CatCh-GFP in mice and in foveal area in primate retinas. Confocal stacks through the RGC layer were acquired using the 20×.

MEA Recordings of Isolated Retinas

Mice were anesthetized and sacrificed by quick cervical dislocation, primates received a lethal dose of pentobarbital. Eyeballs were removed and placed in Ames medium (Sigma Aldrich A1420) bubbled with 95% $O_2$ and 5% $CO_2$ at room temperature. Isolated retinas were placed on a cellulose membrane and gently pressed against an MEA (MEA256 100/30 iR-ITO, Multichannel systems, Germany), with the RGCs facing the electrodes. The retina was continuously perfused with bubbled Ames medium at 34° C. at a rate of 1-2 ml/min during experiments. Metabotropic glutamate receptor agonist L-(+)-2-Amino-4-phosphonobutyric acid (LAP-4, Tocris Bioscience, cat No. 0103) and Glycine receptor antagonist strychnine hydrochloride (Sigma Aldrich S8753) were freshly diluted to concentrations of 50 µM and 10 µM respectively and were bath-applied through the perfusion system 10 minutes prior to recordings. Full-field light stimuli were applied with a Polychrome V monochromator (Olympus) driven by a STG2008 stimulus generator (MCS). Output light intensities were calibrated to range from $1\cdot10^{14}$ photons/cm$^2$/s to $1\cdot10^{17}$ photons/cm$^2$/s. Stimuli were presented for two seconds, with ten-second intervals. Wavelength sensitivity of responses was determined by stimulating ten times, from 400 nm to 650 nm, with 10 nm steps. The order of the tested wavelengths was randomized in order to prevent any adaptation of the retina.

Raw extracellular RGC activity was amplified and sampled at 20 kHz. Resulting data was stored and filtered with a 200 Hz high pass filter for subsequent offline analysis using Spike2 software v.7 (CED Co, UK). Single unit raster plots were obtained using a combination of template matching and cluster grouping based on principal component analysis of the waveforms. In our population analysis, significant responses were determined based on a z-score analysis. We estimated the mean and standard deviation of the activity prior to stimulus and considered that a response was detected if the activity exceeded the mean by more than four times the standard deviation in the 2 s after the onset or the offset of the stimulus (for a bin size of 50 ms). Error bars were calculated over the different experiments. For the responses to light at different wavelengths, we measured the response to each flash in a 1 s window after the stimulus. We then normalized the response of each cell by its maximum firing rate response. For the responses to light at different intensities, we estimated the error bars by bootstrapping over the set of recorded cells.

Two-Photon Imaging and Patch Clamp Recordings

A custom-made two-photon microscope equipped with a 25× water immersion objective (XLPLN25×WMP/NA1.05, Olympus) with a pulsed femto-second laser (InSight™ DeepSee™—Newport Corporation) was used for imaging CatCh-GFP-positive retinal ganglion cells. AAV-treated retinas from rd1 mice were isolated in oxygenized (95% $O_2$, 5% $CO_2$) Ames medium (Sigma-Aldrich). For live two-photon imaging, retinal slices (300 μm) were cut with a razor blade tissue chopper (Stoelting), placed in the recording chamber of the microscope, and z-stacks were acquired using the excitation laser at a wavelength of 930 nm. Images were processed offline using ImageJ. During imaging, the retina was superfused with oxygenized Ames medium.

We used an Axon Multiclamp 700B amplifier for whole-cell recordings. Patch electrodes were made from borosilicate glass (BF100-50-10, Sutter Instruments) and pulled to 8-10 MΩ. Pipettes were filled with 112.5 mM CsMeSO4, 1 mM Mg SO4, $7.8 \times 10^{-3}$ mM CaCl2, 0.5 mM BAPTA, 10 mM HEPES, 4 mM ATP-Na2, 0.5 mM GTP-Na3, 5 mM lidocaine N-ethyl bromide (QX314-Br) (pH 7.2). Cells were clamped at a potential of −60 mV to isolate excitatory currents.

In-Vivo Recordings in the Visual Cortex

Mice were sedated with a low dose of ketamine-xylazine injection (ketamine: 100 mg/kg and xylazine: 10 mg/kg) and then anesthetized with urethane (1.0 g/kg, 10% w/v in saline). Animals were placed in a stereotaxic holder. The temperature was maintained at 37° C. and a coverslip covered with vitamine A (Allergan) was placed on both eyes to prevent corneal dehydration. A craniotomy (1 $mm^2$) above V1 in the contralateral hemisphere to the treated eye was centered 3 mm lateral and 0.5 mm rostral from the lambda point. The dura was removed and an electrode was inserted using a 3-axis micromanipulator (Sutter Instruments) with a 30° angle to the cortical surface. It was advanced 800 μm and the exposed surface was covered with agarose (1.2% in cortex buffer).

Visual stimuli were generated by a 470 nm collimated LED (model M470L3, Thorlabs) placed at 1 cm from the eye. An isolating cone ensured that the illumination was restricted to the stimulated eye. Linear multisite silicon microprobes (sixteen electrodes at 50 μm intervals) were used for recordings. For each acquisition, after averaging over the 200 trials, the electrode showing the VEP with maximal peak amplitude was selected for quantification. The stimulation consisted of 200 ms pulses of blue light repeated 200 times at 1 Hz triggered by a Digidata (Axon). Signals were analysed in Matlab using custom scripts. For local field potentials, signals were low pass filtered at 300 Hz and averaged over the 200 trials.

In Vivo Imaging and Ophthalmic Exams in Non-Human Primates

Fluorescent images of GFP (Fundus Autofluorescence mode: excitation wavelength of 488 nm and barrier filter of 500 nm) and infrared pictures of eye fundus and OCT images were acquired using a Spectralis HRA+OCT system (Heidelberg Engineering, Heidelberg, Germany) after pupil dilation. Ophthalmic exams consisting of slit lamp biomicroscopy (Portable Slit Lamp model SL-14, Kowa) and indirect ophthalmoscopy (Indirect Binocular Ophthalmoscope model HK 150-1 uno, Heine) were performed on all macaques before dosing, at 2 weeks and then on monthly basis.

Histopathological Studies on Macaque Retina

The eye from a NHP injected with the high dose was enucleated at 3 months post-injection a needle was inserted and 0.15-0.3 ml of fixative was injected, until the eyeball became turgid. Eye was immersion fixed in fixative overnight and processed for making horizontal cross-sections across the entire structure. A retinal cross-section presenting all of the desired ocular structures was then imaged on a Nanozoomer (Hamamatsu, Japan).

Example 1

Promoter Sequence of hSNCG

The SNCG gene is located on chromosome 10 (10q23.3) (FIG. 1). It contains 5 exons extending over 3.5 kb from +1 transcription site to the end of the 5th exon. The 1st exon of the multimerine 2 gene (MMRN2) is located 863 bp downstream of +1 SNCG transcription site. In order to extract the human sequence of the SNCG promoter, the −785 to +163 region (indicated by arrows in FIG. 1) was amplified from HEK 293T cells.

The amplification primers were the followings:

```
Forward primer:
                                      (SEQ ID NO: 2)
5'-CACAAGCCAGTTCCTGTCC-3',
and Reverse primer:
                                      (SEQ ID NO: 3)
5'-GGGTGTGCAGGGTTGTG-3'.
```

The promoter sequence was amplified by 30 successive cycles consisting of a 30 second denaturation step at 94° C., followed by a one minute annealing step at 54° C., and an elongation step of one minute at 72° C.

The PCR product (SEQ ID NO: 1) was then subcloned into the pENTR-D/TOPO plasmid by the method using DNA topoisomerase I and sequenced. The sequence was confirmed being identical to the sequence published in Genbank under the Gene ID number 6623.

From this plasmid, the inventors produced AAV vectors and lentiviral vectors derived from HIV-1, expressing the GFP reporter gene under control of the promoter of SEQ ID NO: 1 (FIG. 1).

Construction and Production of AAV-2/Y444F Vectors Comprising mPGK or hSNCG Promoter and a Nucleic Acid Encoding GFP Protein Construction SNCG promoter (SEQ ID NO: 1) and PGK promoter sequences were introduced, by homologous recombination using the Gateway method, in a shuttle plasmid for AAV production containing from 5'ITR to 3'ITR: the Rfa insert (allowing homologous recombination with the Gateway system), a cDNA encoding GFP, and the polyadenylation signal of bovine growth hormone (bGH polyA).

This vector was pseudotyped with a serotype 2 capsid having a point mutation resulting in the substitution Y444F. The mutation was introduced by directed mutagenesis from a packaging plasmid encoding the rep and cap genes of AAV2.

Production

AAV particles were produced by co-transfection (using calcium phosphate co-precipitation) of HEK-293T cells with a plasmid carrying the recombinant AAV2 genome containing the expression cassette, a packaging plasmid expressing rep2 and cap2-Y444F genes, and a helper plasmid. AAV particles were then purified and concentrated from the cytoplasmic extracts of the transfected cells by discontinuous iodixanol gradient ultracentrifugation. Virus titer was measured by quantitative PCR amplification of the ITR sequences of the genomic DNA of AAV particles.

Example 2

C57BL6/J adult mice (6 weeks) received an intravitreal injection of AAV-2/Y444F vectors comprising the promoter of SEQ ID NO: 1 and a nucleic acid encoding GFP protein (cf. example 1 and FIG. 1) diluted at a dose of $10^{11}$ vg (vector genome) in PBS. One month after injection, the fundus and the retina had a normal appearance, indicating the lack of toxicity of the vector or the surgical procedure (FIG. 2A).

Figure 2:
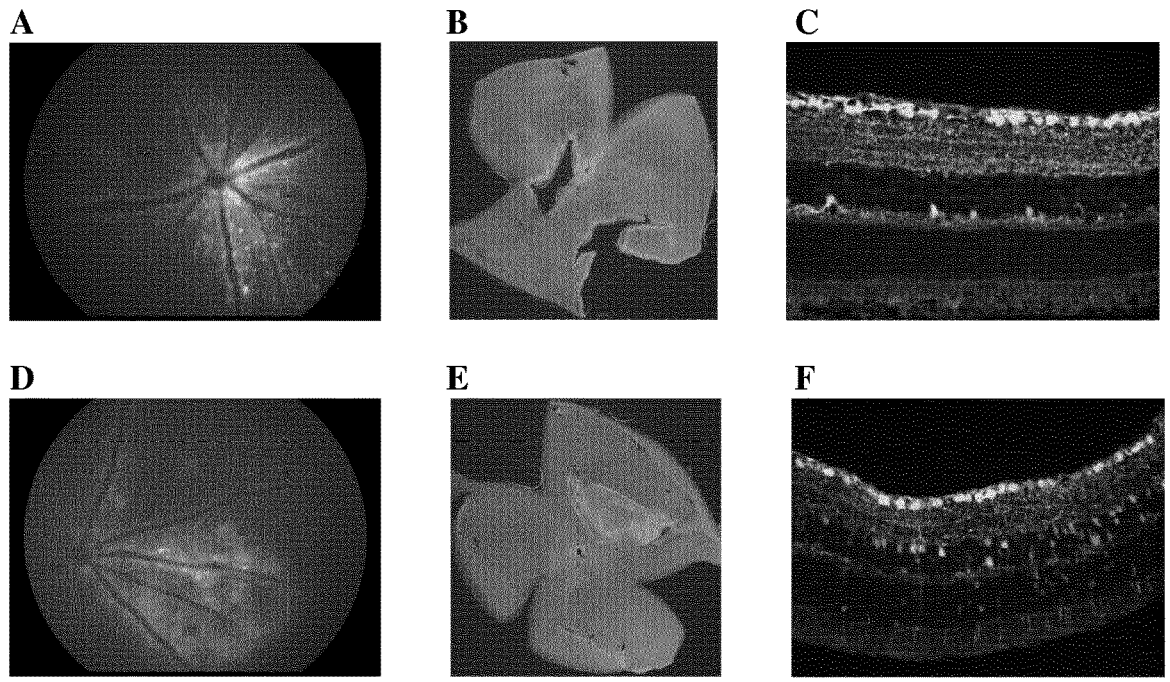
FIG. 2. Top panel: The hSNCG promoter leads to high expression in mouse RGC. Fundus image (A), retinal flat mounts (B) and cryostat section (C) of mouse retinae four weeks after intravitreal injection of AAV2-y444f-hSNCG-GFP. Bottom panel: The PGK promoter leads to high expression across multiple cell types in the retina. Fundus image (D), retinal flat mounts (E) and cryostat section (F) of mouse retinae four weeks after intravitreal injection of AAV2-y444f-PGK-GFP.

The expression of GFP reporter gene in the retina was observed by in vivo imaging of the fundus with direct fluorescence (FIG. 2A). Animals were anesthetized by intraperitoneal injection of a mixture of ketamine and xylazine, and the pupils were dilated by topical application of neosynephrine and mydriaticum. After total pupil dilation, the animals were examined by a fluorescence camera specially designed to view the rodent fundus (MicronIII, PhoenixLaboratories).

With the fluorescence, numerous cell bodies expressing GFP were detected, and nerve fibers converging towards the papilla or the optic nerve head were also observed (not shown). The presence of these nerve fibers demonstrated that GFP was expressed in the RGC.

Example 3

In order to characterize the expression pattern of the hSNCG promoter in the retina, the inventors have compared the hSNCG promoter (SEQ ID NO: 1) to the mPGK promoter, a ubiquitous promoter known to provide a high level of expression in the retina.

Two groups of C57BL6/J mice were injected intravitreally with AAV2-Y444F vectors diluted in PBS at a dose of $10^{11}$ vg and encoding GFP under the control of mPGK or hSNCG promoter. One month after injection, the GFP expression was analyzed in vivo as described above. Animals were then euthanized and tissues fixed by intracardiac perfusion of a solution containing 4% paraformaldehyde in PBS. The eyeballs were subsequently extracted, post-fixed one hour in the same fixative, cryoprotected in a solution containing 25% sucrose in PBS, and then cut with a cryostat to a thickness of 16 µm. GFP expression was then analyzed under a microscope by visualization of direct fluorescence and after immunolabeling using Bnr3a as specific marker of ganglion cells.

In mice injected with an AAV vector comprising the ubiquitous promoter mPGK, there were a large number of transduced cells in the RGC layer, but also at the bipolar cell layer (INL) and the photoreceptor layer (ONL) (FIG. 2F). Cells having the morphology of photoreceptors or Miller cells were also clearly detected. In addition, the location of transduced cells in the INL suggests that bipolar or amacrine neurons are also transduced.

In mice injected with an AAV vector comprising the promoter of SEQ ID NO: 1, the RGC were very strongly marked. GFP was detected in their cell bodies and their dendritic arborization at the inner plexiform layer revealing the laminar organization of these ramifications (FIG. 2C). Except for few horizontal cells, the expression of GFP was restricted to the ganglion cell layer.

Example 4

We evaluated strength and specificity of gene expression in RGCs by investigating localization of expression by co-labeling with Brn3a. Brn3a is specifically expressed in RGCs and antibodies against this transcription factor are considered a reliable marker to identify murine RGCs (Quina et al. J. Neurosci. 2005; 25(50):11595-11604).

Two groups of C57BL6/J mice were injected intravitreally with AAV2 vectors diluted in PBS at a dose of $10^{11}$ vg and encoding GFP under the control of CMV or hSNCG promoter. One month after injection, animals were euthanized and tissues fixed by intracardiac perfusion of a solution containing 4% paraformaldehyde in PBS. The eyeballs were subsequently extracted, post-fixed one hour in the same fixative, cryoprotected in a solution containing 25% sucrose in PBS, and then cut with a cryostat to a thickness of 16 µm. GFP expression was then analyzed under a microscope by visualization of direct fluorescence and after immunolabeling using Bnr3a as specific marker of ganglion cells.

Figure 3:
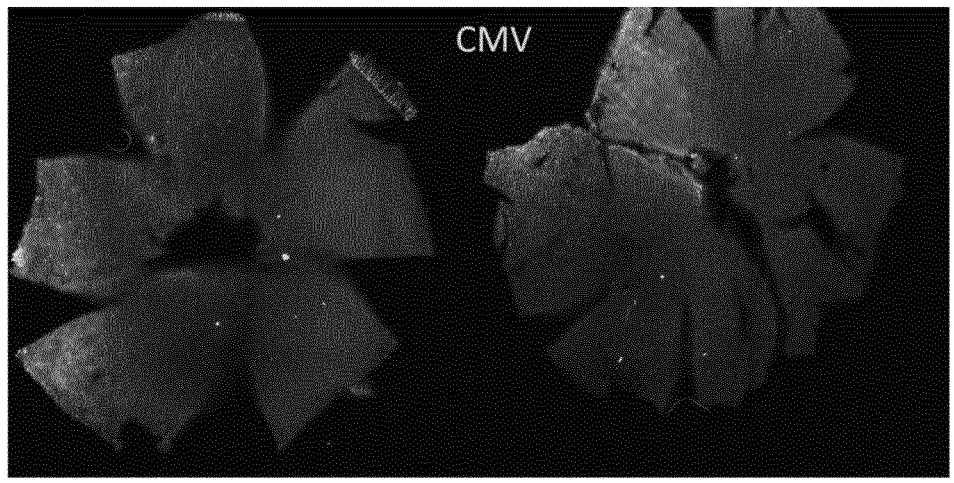
FIG. 3. Confocal microscopy images of retinal flat mounts of mouse retinae after intravitreal injection of AAV2-CMV-GFP (top) and AAV2-hSNCG-GFP (bottom) (A) and cross-sections (B) of mouse retinae after intravitreal injection of AAV2-hSNCG-GFP.
Figure 3:
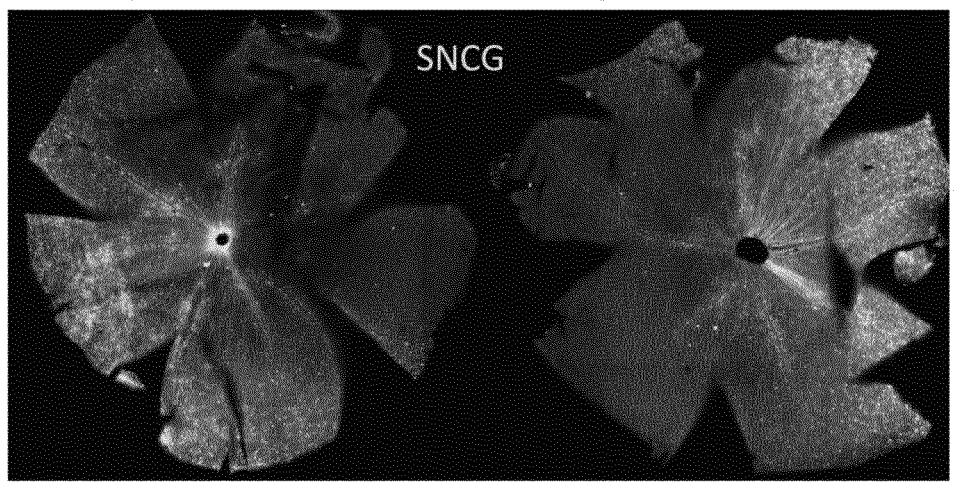
Figure 3:
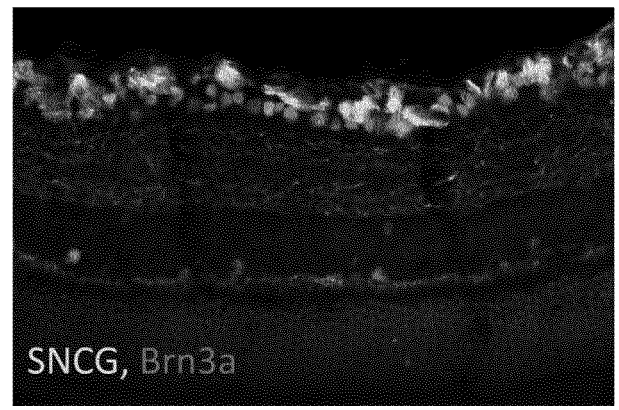

In mice injected with an AAV2 vector comprising the promoter of SEQ ID NO: 1, the RGC were very strongly marked. GFP was detected in their cell bodies and their dendritic arborization at the inner plexiform layer revealing the laminar organization of these ramifications. Confocal microscopy images of cross-sections (FIG. 3B) from SNCG-GFP retinas showed strong GFP expression in RGCs and this expression was highly co-localized with the Bnr3a labeling.

Example 5

Figure 4:
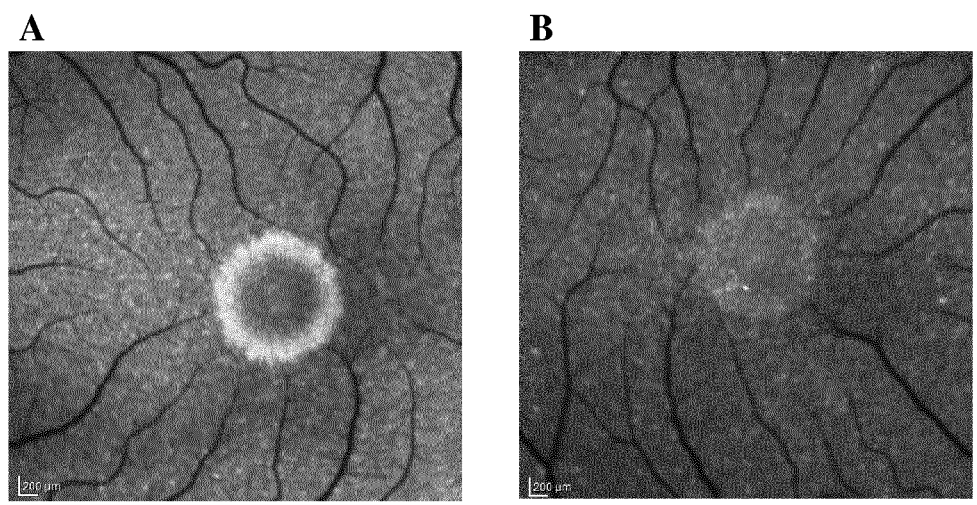
FIG. 4. Evaluation of GFP expression in macular region of cynomolgus macaque retinas by fundus fluorescence imaging. AAV-GFP vectors containing the SNCG promoter (A), CMV promoter (B) were administered by intravitreal injection. Areas with GFP expression appear white on a dark background. The camera automatically adjusts the exposure time, and image on FIG. 4A with the greatest intensity of GFP expression has the darkest background color but for image on FIG. 4B with the weakest intensity of GFP expression there is little difference between the transduction area (peri-foveal ring) and the background.

$5 \times 10^{11}$ viral particles of each AAV2-CMV-GFP or AAV2-SNCG-GFP vector were injected intravitreally into the eyes of a normal macaque (*Macaca fascicularis*) in a volume of 100 µL. We evaluated GFP expression in cynomolgus macaque retinas by fundus fluorescence imaging. Fluorescent images of GFP (Fundus Autofluorescence mode: excitation wavelength of 488 nm and barrier filter of 500 nm) were acquired using an Spectralis HRA+OCT system (Spectralis HRA+OCT; Heidelberg Engineering, Heidelberg, Germany) after pupil dilation. Fluorescence images showed a greatest intensity of GFP expression between the transduction area (peri-foveal ring) and the background with AAV-GFP vectors containing the SNCG promoter (FIG. 4A) than with the CMV promoter (FIG. 4B). This experiment demonstrates that higher transgene expression is obtained in non-human primates using the SNCG promoter (SEQ ID NO: 1).

Example 6

Strong, RGC-Specific Expression in the Mouse Retina Using the Promoter Sequence of SEQ ID NO:1.

The promoter sequence obtained in example 1 from the regulatory region of human gamma synuclein (SNCG) (SEQ ID NO: 1), was cloned upstream of GFP. We characterized AAV mediated expression patterns in the retina of mice and saw high-level GFP expression in RGCs. We then cloned this sequence upstream of humanized CatCh (human codon-optimized channelrhodopsin bearing the L132C mutation) in an AAV backbone. AAV2 vectors were produced with either CMV or SNCG promoter driving the expression of hCatCh in fusion with GFP. Five rd1 mouse eyes were injected with either CMV or SNCG driving expression of hCatCh-GFP.

Figure 5:
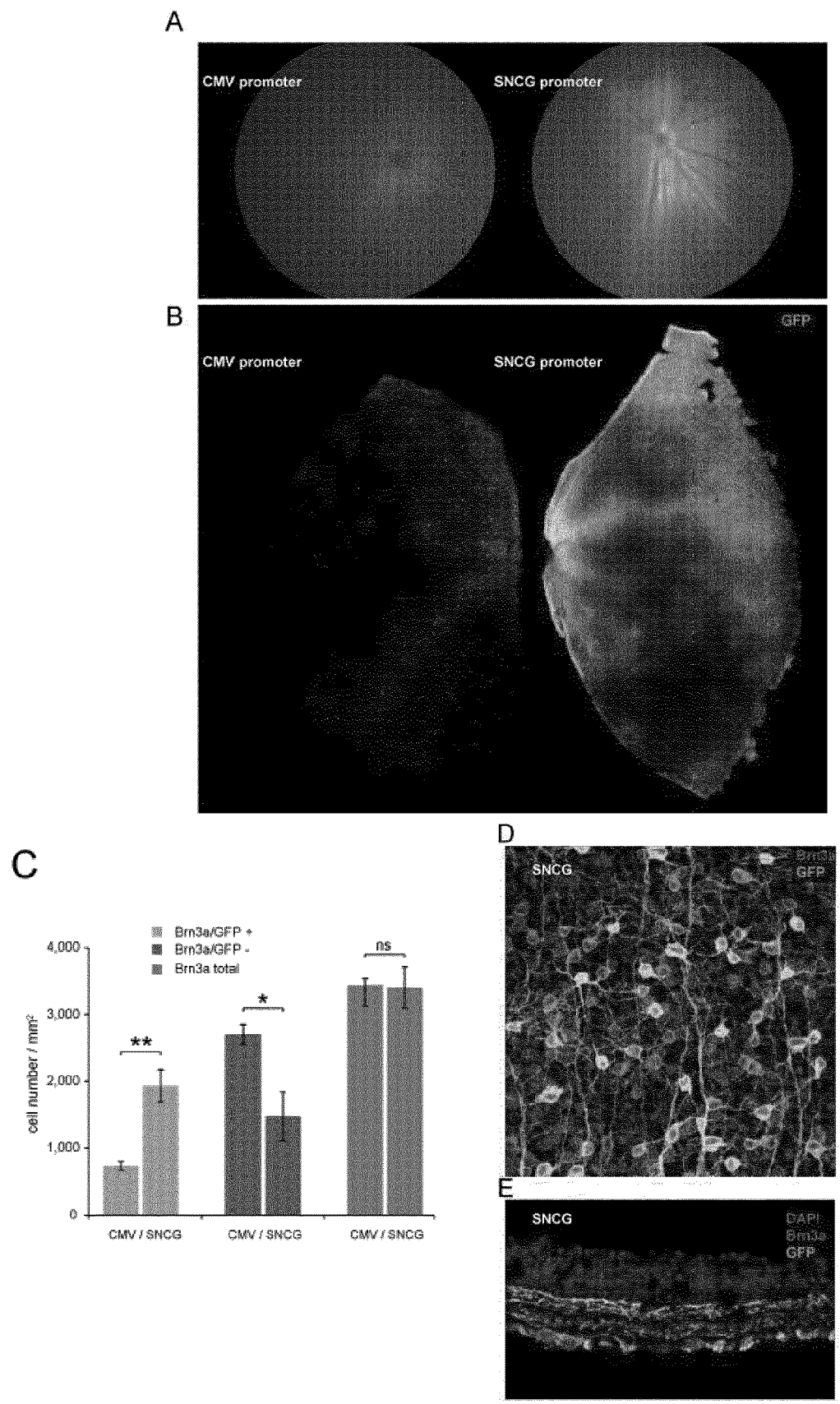
FIG. 5. SNCG promoter drives higher-level hCatCh-GFP expression than CMV promoter in mouse RGCs. A) Fundus image of representative rd1 mouse retinae injected with $5 \times 10^9$ vg of either AAV2-SNCG-hCatCh-GFP (right) or AAV2-CMV-hCatCh-GFP (left). B) Retinal flat-mounts obtained from the same injection series showing CatCh-GFP fluorescence obtained under the SNCG promoter (right) and the CMV promoter (left). C) Quantification of Brn3a-positive, GFP-positive and double labeled cells in rd1 mouse retina injected with either AAV2-SNCG-hCatCh-GFP or AAV2-CMV-hCatCh-GFP. Confocal stack projections across the ganglion cell layer for cell counts over chosen fields in the central and in peripheral regions of the retina. Regions were chosen in each quadrant and cell-counts were averaged to obtain Brn3a-positive, GFP-positive and co-labeled cells per $mm^2$. Error bars represent SEM. D) Representative confocal stack projection across the RGC layer of rd1 mouse retina transduced with SNCG-CatCh-GFP, co-labeled with Brn3a (red) and anti-GFP (green) antibodies. E) Cross-sections obtained from one representative retinal flat-mount in the SNCG-CatCh-GFP injected retinas co-labeled with Bnr3a and anti-GFP and nuclei were labeled with DAPI.

Fluorescent fundus images showed higher fluorescence in all eyes injected with SNCG with respect to eyes injected with CMV (FIG. 5a). Eyes were enucleated 8 weeks after injection and retinal flat-mounts corroborated higher intensity fluorescence with SNCG promoter compared to CMV (FIG. 5b). We evaluated strength and efficacy of gene expression in RGCs by investigating localization of expression by co-labeling with Brn3a (FIG. 5c). Brn3a is specifically expressed in RGCs and antibodies against this transcription factor are considered a reliable marker to identify and quantify murine RGCs (Quina et al. J. Neurosci. 2005; 25(50):11595-11604). Confocal microscopy images of retinal flat-mounts (FIG. 5d) and cross-sections (FIG. 5e) from SNCG-CatCh-GFP retinas showed strong GFP expression in RGCs and this expression was highly co-localized with the Bnr3a labelling. In cell quantification of such images, we showed that the Brn3a antibody labels an equal number of RGCs on retinas transfected with either the SNCG or CMV promoter. In SNCG retinas, 57% of these Brn3a-positive RGCs were also expressing GFP whereas this proportion decreased to 21% in the CMV retinas (FIG. 5c). The difference between SNCG and CMV retinas was statistically significant. This greater ratio of GFP-expressing Brn3a-positive RGCs demonstrated the greater efficacy of SNCG promoter (SEQ ID NO: 1) to drive high-level gene expression in RGCs.

Retinal and Cortical Responses Following CatCh Expression in RGCs of the Rd1 Retina Under the SNCG Promoter of SEQ ID NO: 1

Figure 6:
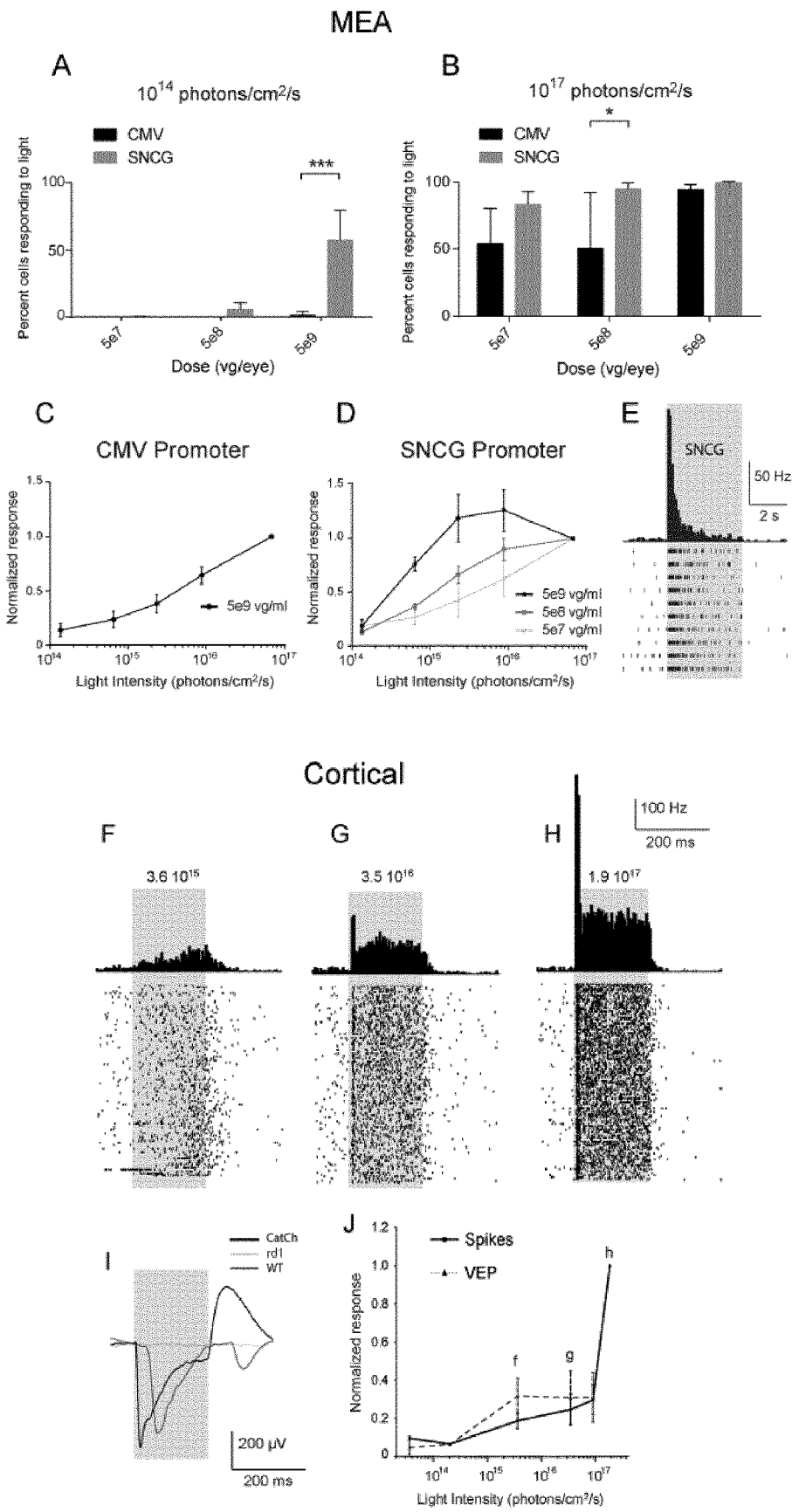
FIG. 6. Functional CatCh responses in the retinas and cortex of rd1 mice. Percentages of cells with a spontaneous activity showing a light response at 480 nm under either A) $10^{14}$ photons/$cm^2$/s or B) $10^{17}$ photons/$cm^2$/s in retinas expressing CatCh under control of CMV (black) or SNCG (grey) at $5 \times 10^7$, $5 \times 10^8$ and $5 \times 10^9$ vg per eye (n=4). C) Response amplitude (normalized to the response obtained at maximum luminance) as a function of light intensity in retinas expressing CatCh under control of CMV promoter at $5 \times 10^9$ viral particle dose (n=4, 155 cells) D) Response amplitude (normalized to the response obtained at maximum luminance) as a function of light intensity in retinas expressing CatCh under control of SNCG promoter at $5 \times 10^7$ viral particle dose (light grey, n=4 retinas, 158 cells), $5 \times 10^8$ (dark grey, n=4 retinas, 221 cells) and $5 \times 10^9$ (black, n=4 retinas, 261 cells) viral particles (vg) per eye. E) Raster plots and peri-stimulus time histogram (PSTH) showing the light response or increase in spike frequency during full field flashes at 480 nm in a retina expressing CatCh under control of the SNCG promoter. Note that with the SNCG promoter that the curve is reaching a plateau at the maximum AAV vector dose. (F, G, H) PSTHs (top) and corresponding raster plots (bottom) of visual cortex neurons of rd1 mice expressing SNCG-CatCh in response to 475 nm full field flashes at 3 different increasing light intensities ($10^{15}$, $10^{16}$ and $10^{17}$ photons/$cm^2$/s). I) Comparison of Visually Evoked potentials (VEPs) recorded in SNCG-CatCh treated rd1 retinas with the $5 \times 10^9$ vg dose, compared to untreated rd1 retinas and wild-type mouse retinas. J) Normalized cortical activity (spikes and VEP) as a function of light intensities at 475 nm (n=3 mice). Error bars represent SEM.

To demonstrate that selective RGC targeting of hCatCh-GFP can restore visual function in blind rd1 retinas (age >12 weeks), we recorded spiking activity from retinal ganglion cells using a multi-electrode array (MEA). Mice injected 4-8 weeks after birth with 3 doses of AAV2 encoding hCatCh-GFP either under CMV or SNCG (SEQ ID NO: 1) promoter and MEA recordings were performed 8-12 weeks after injection (FIG. 6 a-e). Light sensitivity of the optogenetic responses were measured as a readout on a 252-electrode array in light conditions ranging from $10^{14}$ to $10^{17}$ photons/cm$^2$/s. Light evoked spiking activity was observed when stimulating treated rd1 retinas with 2 second full-field flashes (FIG. 6 a-e), whereas control rd1 retinas did not show any increase in spiking activity in response to light (data not shown). Percentage of cells responding to light was dependent on viral dose (FIG. 6 a-b). Greater number of cells responded in rd1 animals injected with the SNCG promoter at the highest AAV dose at $10^{14}$ photons/cm$^2$/s, (FIG. 6a). This improved sensitivity corroborates that SNCG promoter (SEQ ID NO: 1) drives higher-level CatCh expression in RGCs and thus a higher percentage of cells become light responsive for the same viral load. Firing rate frequency was intensity dependent, giving rise to robust light-responses at $10^{14}$ photons/cm$^2$/s for CatCh expressed under SNCG promoter at a viral dose of 5×10$^9$ vg per eye (FIG. 6a). The normalized firing rate increased with rising light intensities (FIGS. 6c-d). Note that only the highest viral dose with the CMV promoter generated responses to light at $10^{14}$ photons/cm$^2$/s (FIG. 6a). Furthermore, very few cells were responding to light in these conditions. Even at the highest light intensity, less cells were responding in the intermediate viral dose (5×10$^8$ vg per eye) (FIG. 6b). This experiment demonstrated the greater efficacy of the SNCG promoter (SEQ ID NO: 1) to drive expression of a functional protein in RGCs.

To demonstrate that this RGC activation was transmitted to the brain, we recorded the light responses at the cortical level upon retinal stimulation in vivo. For this experiment, another series of rd1 mice were injected with AAV2-SNCG-hCatCh-GFP and we used them to record spiking activity and local field potentials (VEPs) in the visual cortex in response to increasing light intensities. RGC responses translated to highly light-sensitive activity in the visual cortex (FIGS. 6f-j). The treated eye (contralateral to the recording hemisphere) was stimulated with 200 ms pulses of blue light (with light intensities up to 1.7 10$^{17}$ photons/cm$^2$/s) repeated 200 times at 1 Hz (FIGS. 6f-h). No VEPs were visible (flat traces) on recordings from untreated rd1 mice. When compared to VEPs measured on wild-type mice, CatCh-driven VEPs had slower latencies (FIG. 6i). A shorter latency is expected because the phototransduction cascade and subsequent retinal computation are bypassed. FIG. 6f-h and j illustrate the intensity dependence of spiking responses with the progressive apparition of a prominent peak of shorter latency at higher light intensities. The latency of the spikes in CatCh-treated rd1 mice was again shorter (10.1+/−2 ms, n=3) than the mean ON latency in wild-type mice (52.98+/−3.83 ms, n=3). These responses correlated strictly with the duration of the light stimulation and were a result of the CatCh-elicited RGC activation. These functional results clearly demonstrate that AAV-driven expression of CatCh under the SNCG promoter can activate RGCs in the blind mouse retina to restore light sensitivity and that these cells transmit light signals to the brain up to the visual cortex.

In Vivo Inflammatory Responses in NHP Eyes

In mouse studies, we used doses ranging from 5×10$^7$ to 5×10$^9$ vg/eye. We observed that using low light intensities required for minimizing phototoxicity in humans ($10^{14}$-$10^{15}$ photons/cm$^2$/s range), the particle number necessary to obtain light responses on MEA were in the 5×10$^8$ to 5×10$^9$ vg/eye range. Since the volume of the macaque vitreous is about 100 times greater than the vitreous volume of a mouse, we decided to use the pharmacological equivalent of this dose range in our non-human primate experiments. Five non-human primates were chosen based on absence of neutralizing antibody titers against AAV2 in their blood sera (Kotterman et al. Gene Ther. 2015 February; 22(2):116-26). Four of these adult macaques were injected intravitreally with either 1×10$^{11}$ (n=4 eyes) or 5×10$^{11}$ particles (n=4 eyes) of AAV2 encoding hCatCh under SNCG promoter (Table 1).

TABLE 1

Injections in non-human primates: animal number, AAV vector and viral dose injected intravitreally

| NHP # | | AAV vector | Dose (vg/eye) | |
|---|---|---|---|---|
| NHP 1 | -Right eye | AAV2-SNCG-hCatCh-GFP | 1 × 10$^{11}$ | 3 months group |
| | -Left eye | AAV2-SNCG-hCatCh-GFP | 5 × 10$^{11}$ | |
| NHP 2 | -Right eye | AAV2-SNCG-hCatCh | 5 × 10$^{11}$ | |
| | -Left eye | AAV2-SNCG-hCatCh | 5 × 10$^{11}$ | |
| NHP 3 | -Right eye | AAV2-SNCG-hCatCh | 5 × 10$^{11}$ | |
| | -Left eye | AAV2-SNCG-hCatCh | 5 × 10$^{11}$ | |

TABLE 1-continued

Injections in non-human primates: animal number, AAV vector and viral dose injected intravitreally

| NHP # | | AAV vector | Dose (vg/eye) | |
|---|---|---|---|---|
| NHP 4 | -Right eye | AAV2-SNCG-hCatCh | $1 \times 10^{11}$ | |
| | -Left eye | AAV2-SNCG-hCatCh | $1 \times 10^{11}$ | |
| NHP 5 | -Right eye | AAV2-SNCG-hCatCh | $1 \times 10^{11}$ | |
| | -Left eye | AAV2-SNCG-hCatCh | $1 \times 10^{11}$ | |
| NHP 1' | -Right eye | AAV2-CMV-hCatCh-GFP | $1 \times 10^{12}$ | 6 months group |
| | -Left eye | AAV2-CMV-hCatCh-GFP | $1 \times 10^{12}$ | |
| NHP 2' | -Right eye | AAV2-SNCG-hCatCh | $1 \times 10^{12}$ | |
| | -Left eye | AAV2-SNCG-hCatCh | $1 \times 10^{12}$ | |
| NHP 3' | -Right eye | AAV2-SNCG-hCatCh | $5 \times 10^{11}$ | |
| | -Left eye | AAV2-SNCG-hCatCh | $5 \times 10^{11}$ | |
| NHP 4' | -Right eye | AAV2-SNCG-hCatCh | $5 \times 10^{11}$ | |
| | -Left eye | AAV2-SNCG-hCatCh | $5 \times 10^{11}$ | |
| NHP 5' | -Right eye | AAV2-CMV-hCatCh | $5 \times 10^{11}$ | |
| | -Left eye | AAV2-CMV-hCatCh | $5 \times 10^{11}$ | |

As GFP can be immunogenic, in order to distinguish between potential inflammatory responses to GFP and to hCatCh, we used hCatCh with no fluorescent tag. However, one primate was injected with the same two doses (one eye with low dose and the other with high dose), but this time encoding hCatCh in fusion with GFP to monitor gene expression in vivo (NHP1).

Figure 7:
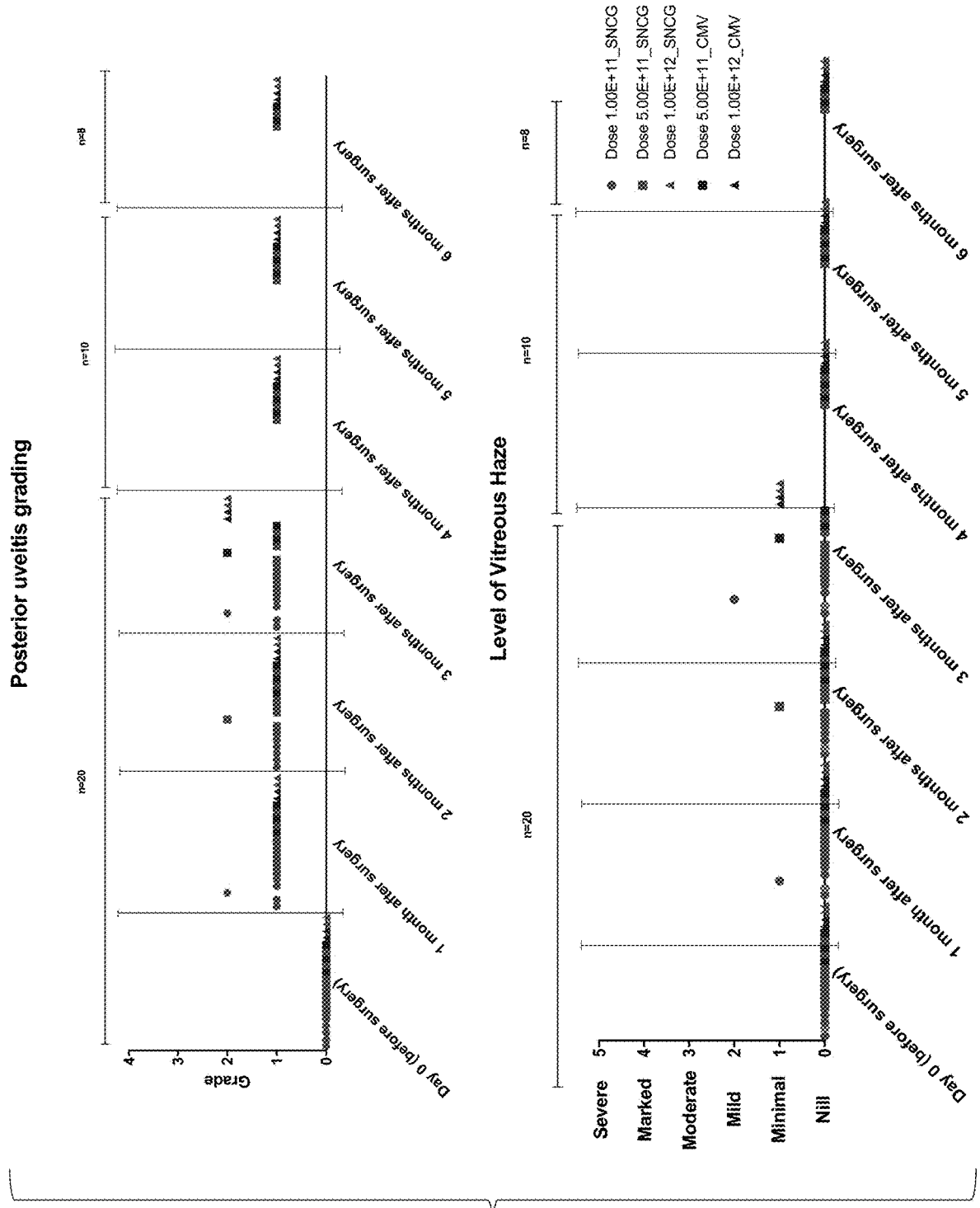
FIG. 7. In vivo ophthalmic exams in AAV-CatCh injected NHPs. A) Grades of posterior uveitis from faint to intense B) Grades of vitreal haze from minimal to severe.

The vitreous remained sufficiently transparent so that there was little progression in the gravity of inflammation as defined in the grading scheme for vitreous haze (FIG. 7 lower panel). Only slight impairment of fundus visualization was detected at one and three months post-injection in one eye in the low dosage group; and at two-three months post-injection in all eyes in the high dosage group (FIG. 7 lower panel).

Assessment by the Posterior uveitis grading (FIG. 7—upper panel) showed persistent presence of cells in the vitreous in all study groups beginning from the first month after injection (FIG. 7—upper panel). At five-six months after injection most of the cells in the vitreous seems to be old.

Quantification and analysis of cells in the vitreous was performed for the intermediate and high dosage groups and showed a two-wave curve of the inflammatory reactivity (FIG. 7). All eyes of both groups reveal the first-wave vitreous inflammatory response at the first month post-injection time-point, and the level of vitreous cells inflammatory reaction was higher in the high dosage group of both viral constructions (the SNCG-Catch and CMV-Catch) and in CMV-Catch construction group with middle dosage group. The same profile but with the lower level was noted in the second wave inflammatory vitreous cells reaction at tree-four months post-injection time-point.

Examination of eye fundus using a slit lamp and indirect ophthalmoscopy revealed no inflammatory sings of the retina, retinal vessels, optic disc and choroid.

The signs of inflammation described above reflect well the natural immunological reaction of the eye to gene therapy. The purpose of this thorough and detailed analysis is to understand the kinetics of the inflammatory response to gene therapy. None of the observed events of the inflammatory reaction throughout of five-six months observation period had significant influence on vision.

Figure 8:
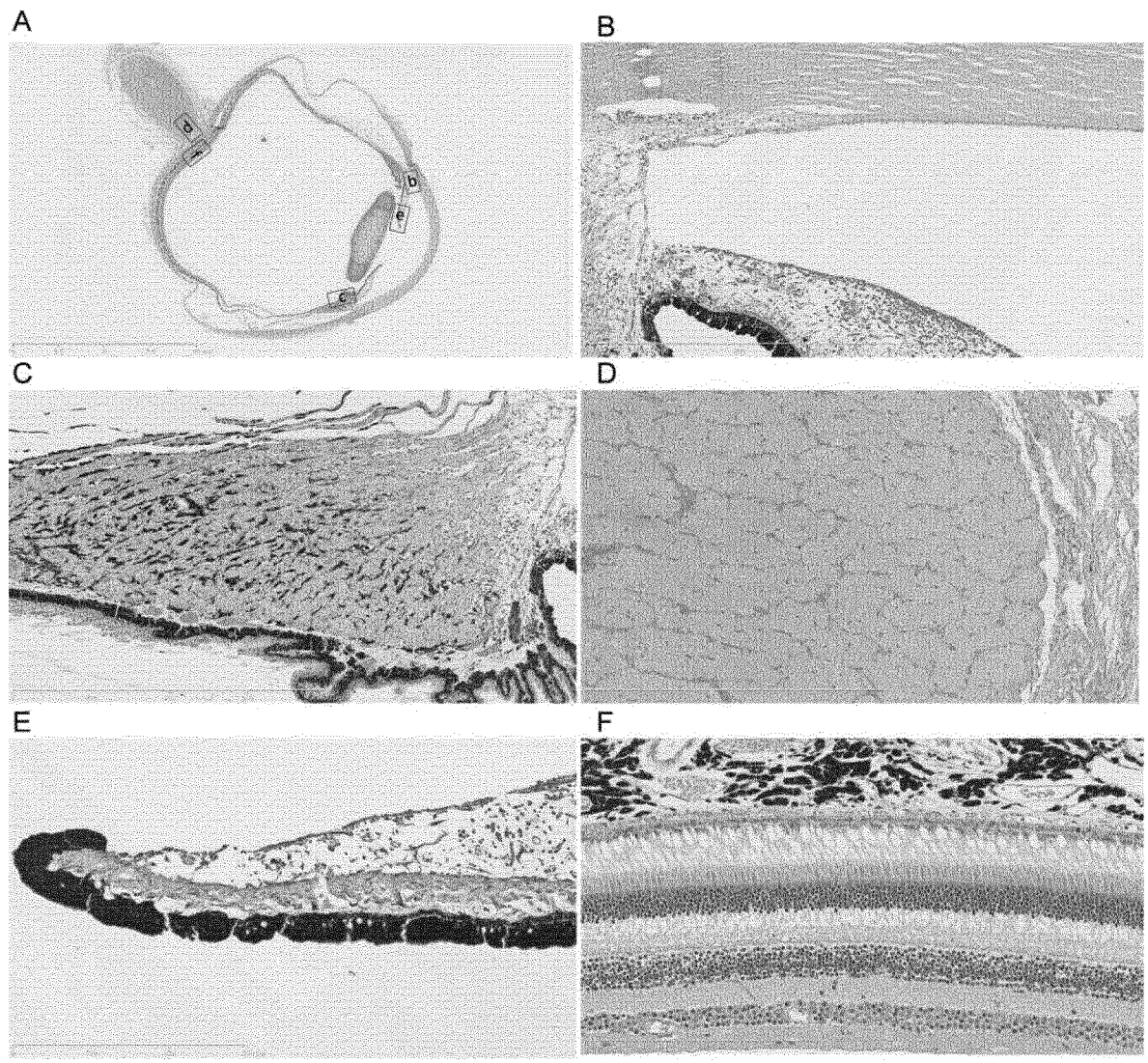
FIG. 8. Histo-pathological examination of the eye from a NHP with high-dose injection of AAV2-CatCh at three months post-injection. A) Retinal slice across the vertical meridian of the eye imaged at a resolution of 40×. (B-F) Absence of detectable lymphocytes, macrophages or damage to ocular structures in the trabecular meshwork (B), ciliary body (C), optic nerve (D), iris (E) and retina (F) on magnified areas from (A).

Histopathological Examination of One Eye from the High Dose Group Shows No Inflammatory Cells No histological lesions were observed in the only eye we analyzed from the high-dose group at 3-months post-injection. The entire eye was fixed, sectioned and observed using nanozoomer technology allowing 40× resolution anywhere within the section (FIG. 8). No structural changes indicative of inflammation (existence of lymphocytes or plasma cells in the trabecular meshwork and the irido-corneal angle, inflammatory cells in the vitreous, or perivascular lymphocytes in the retina) were noted (FIG. 8 b-f). Importantly, this animal (NHP 3) from the $5 \times 10^{11}$ vg dosing group had displayed variable levels of vitreal haze and cells upon indirect ophthalmoscope evaluation at 1-2 months post-injection (FIG. 7). The absence of inflammatory cells and retinal damage at three months indicate that any preceding anterior chamber flare or vitreal haze did not lead to permanent changes in retinal structure and overall the retina and anterior segments of the eye were void of any signs of damage or inflammation. Therefore, optogene expression under the control of SNCG promoter (SEQ ID NO: 1) appears not to induce an inflammatory reaction.

Proportion of CatCh-Expressing RGCs in the Peri Foveal Area of NHPs

Figure 9:
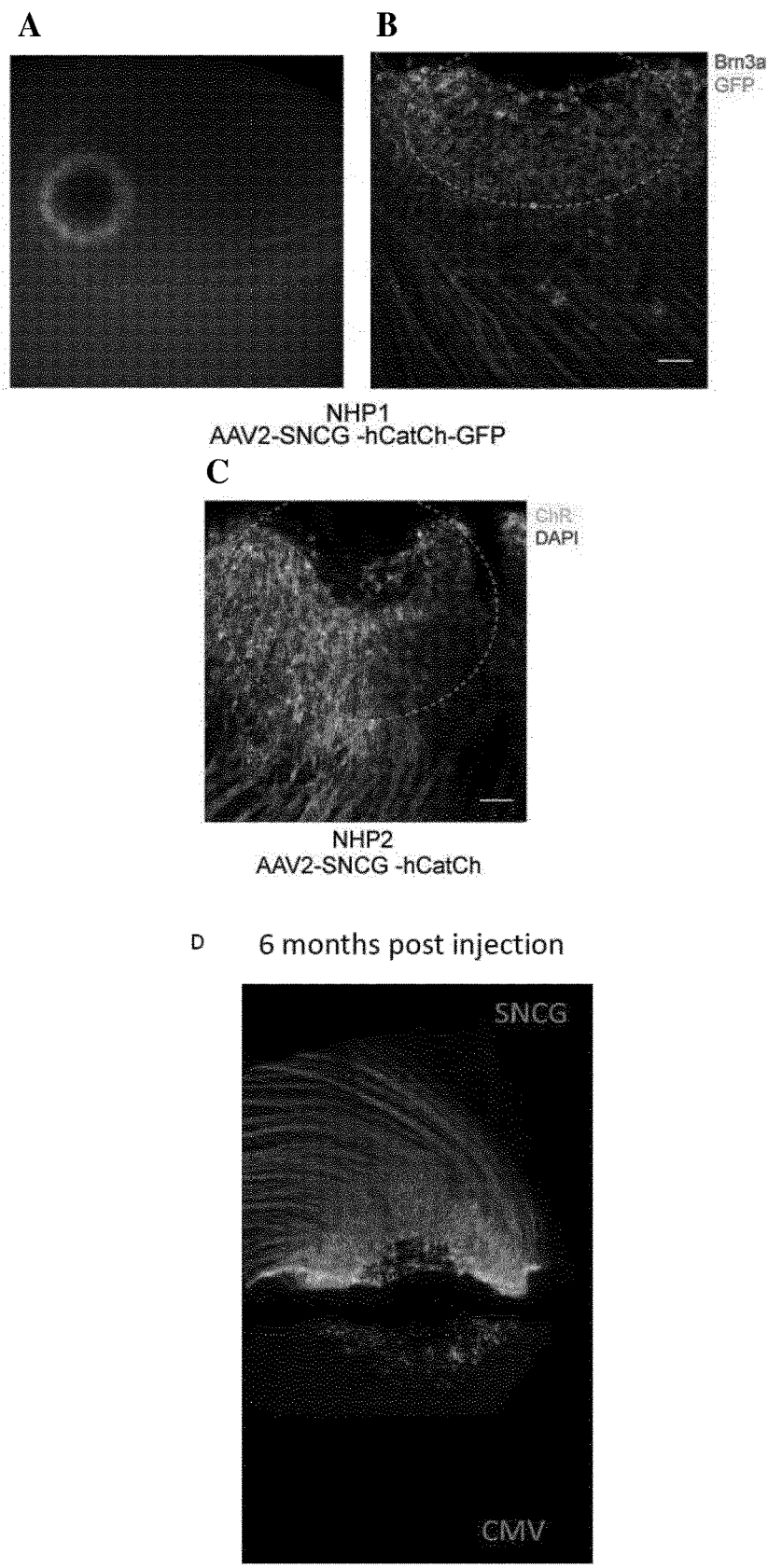
FIG. 9.
A) The macular region of NHP1 prior to dissection showing CatCh expression in the peri-foveolar ring 3 months post-injection. B) Half of the same foveal region after MEA recordings and RGC immunolabelling. Retinal flat-mount has been stained with Brn3a and GFP antibodies. C) The foveal region of retina from another macaque injected at the same dose at 3 months post-injection. Retinal flat-mount has been stained with antibodies against channelrhodopsin. Nuclei have been stained with DAPI. D) A representative section over the fovea of a macaque retina 6 months after injection with AAV2-SNCG-CatCh (upper panel) or AAV2-CMV-CatCh (lower panel) at a dose of 10E12 vg/eye. Retinal flat-mount has been stained with antibodies against channelrhodopsin.

Retinal flat-mounts were then stained with antibodies against channelrhodopsin (Busskamp et al. Science 2010; 3 (June):413-7), Brn3a and GFP (when present) after MEA recordings. Tissue from NHP1 was labeled with anti-GFP antibodies in green and anti-Brn3a antibodies in red (FIG. 9b). This is the only retina where we could use the RGC specific marker, Brn3a, in conjunction with an antibody indicating localization of CatCh as both Brn3a and anti-channelrhodopsin antibodies are produced in the same species. In this tissue spanning a ~1 mm square from the center of the fovea, we counted Brn3a (+) and CatCh-GFP (+) cells in half a cercle with a 600 µm radius around the fovea (FIG. 9b). In this area, around 37% of Brn3a(+) cells were also positive for GFP (523 GFP-positive cells for 1413 Brn3a-positive cells). In the tissue from NHP 2, we counted 1351 CatCh-positive cells for one half of an eye and 455 in the contralateral eye in the region spanning 600 µm from the center of the fovea (FIG. 9c). One of the retinas from the high-dose group was damaged following the MEA recording process and could not be used for immunofluorescence labeling. These results indicate that at least one fourth of peri-foveolar RGCs were labeled with CatCh after an injection with the $5 \times 10^{11}$ vg.

Single-Cell Patch Clamp Recordings Reveal CatCh-Driven Photocurrents in Individual RGCs Around the Fovea NHP 1, injected with AAV2-SNCG-hCatCh-GFP was sacrificed three months post injection. Retinas were dissected and foveal regions were carefully cut in two halves for MEA and patch-clamp recordings because the green fluorescence attributed to GFP was maximal in this area (FIG. 9a). This expression pattern was consistent with previous NHP studies (Dalkara et al. Sci Transl Med. 2013 Jun. 12; 5(189):189ra76; Yin et al. Invest Ophthalmol Vis Sci. 2011 Apr. 25; 52(5):2775-83). In all of our experiments, endogenous light responses in NHP retinas were blocked using a metabotropic glutamate receptor agonist L-(+)-2-Amino-4-phosphonobutyric acid (L-AP4) at 50 µM in the bath solution. We had previously validated the L-AP4 blockade of all ON responses in wild-type retinas in both mouse (Nagel et al. Proc. Natl. Acad. Sci. U.S.A 2003; 100(24): 13940-5) and human retinas (Tomita et al. Mol Ther. 2014 August; 22(8):1434-40).

Figure 10:
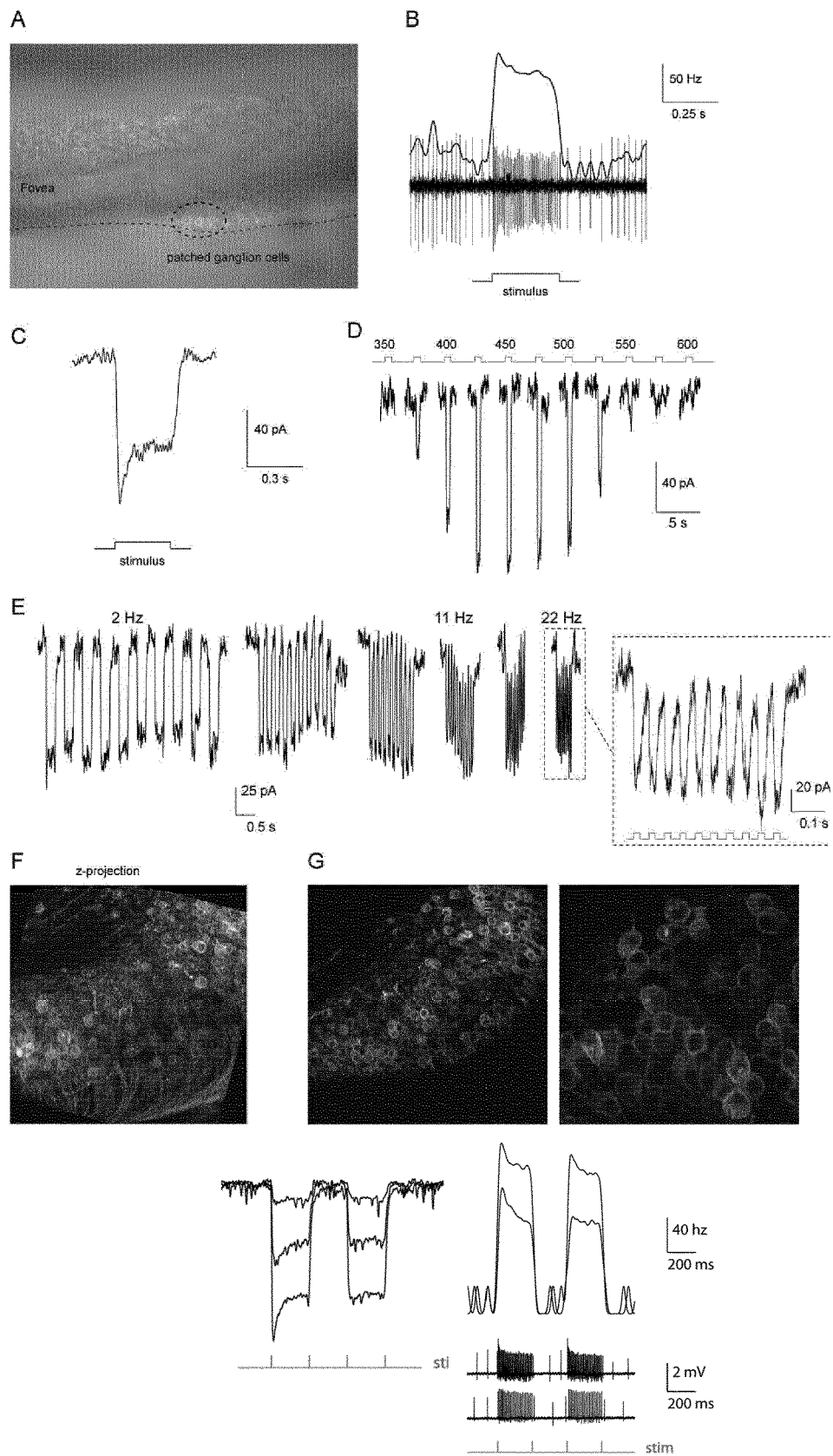
FIG. 10. Characteristics of CatCh-mediated single cell light responses. A) Retinal slice showing the perifoveolar region of NHP 2, injected with AAV2-hCatCh (no GFP tag), where light-responsive ganglion cells were patched. B) RGC recording in the cell-attached mode showing spikes and their increase in frequency during the light stimulation as seen on the curve of spike frequencies above the recording. C) Photocurrent response of a cell patch-clamped at −60 mV. D) Action spectrum of a patched RGC displaying a photocurrent amplitude peak around 450 nm. E) Flicker stimulations at increasing frequencies ranging from 2 to 22 Hz. Cells in (B-E) were recorded from the region shown in (A) at 470 nm with a light intensity of $1.46 \cdot 10^{16}$ photons/cm$^2$/s under L-AP4 perfusion (F-G) Two-photon images of the perifoveolar region of NHP 1, injected with AAV2-hCatCh-GFP displaying the high density of transfected cells with membrane bound expression. H) Responses of 2 representative cells either patch-clamped at −60 mV and displaying photocurrents (left) or recorded in the cell-attached mode and showing an increasing frequency of spikes during light stimulations (right).

At the single cell level, patch-clamp recordings demonstrated light responses under $1.46 \cdot 10^{16}$ photons/cm²/s at 470 nm in RGCs from both AAV2-SNCG-hCatCh and AAV2-SNCG-hCatCh-GFP conditions (n=2 and n=3 cells, respectively) (FIG. 10). AAV2-SNCG-hCatCh RGCs had to be patched without assistance by fluorescent label. All responsive cells were found in a disc (500-600 µm) around the foveal center (FIG. 10a). In some cases, cells recorded in cell-attached configuration displayed fast and robust spiking patterns (FIG. 10b). We observed typical channelrhodopsin-evoked photocurrents consisting of a fast transient current followed by a steady-state one under whole-cell configuration, at a holding potential of −60 mV in presence of lidocaine (FIG. 10c). The photocurrents peaked upon stimulation at 450 nm, remained pronounced up to 500 nm (FIG. 10d) and they were fast enough to follow 22 Hz light-pulses (FIG. 10e). When scanned with a 2-photon laser, CatCh-GFP ganglion cells showed dense, membrane-bound GFP-labeling in the peri-foveolar region (FIG. 10 f-g).

Monkeys injected with AAV2-CMV-hCatCh or AAV2-SNCG-hCatCh at $5\times10^{11}$ or $1\times10^{12}$ vg/dose were sacrificed 6 months after injection. Using single cell recordings techniques (cell-attached and patch-clamp recordings) we were able to record light responses (photocurrent and spiking activity) from all groups, as shown on FIG. 10h with examples obtained with the SNCG group at low dose.

Figure 11:
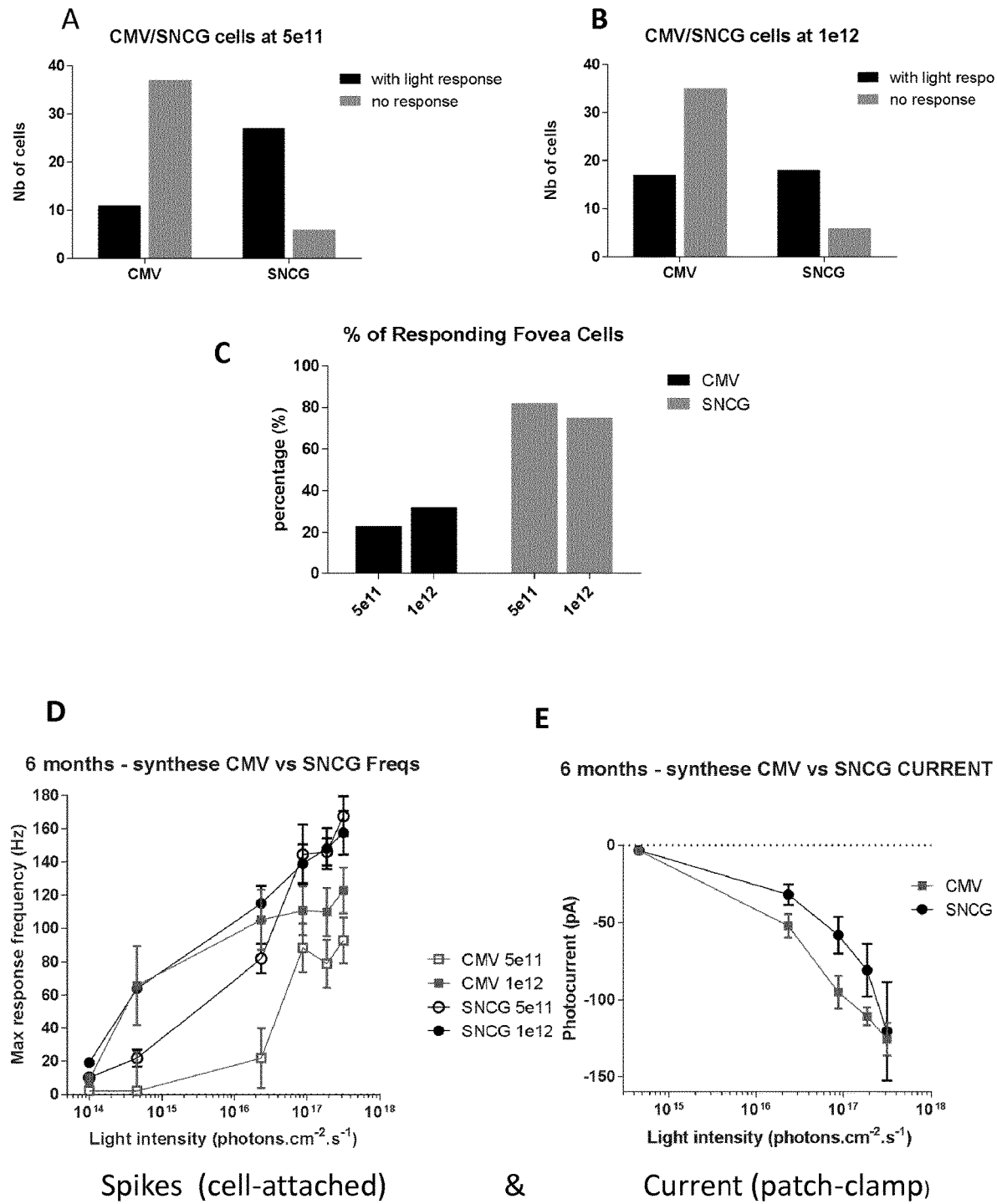
FIG. 11. Single cell recordings (cell-attached and patch-clamp) from RGCs expressing CatCh in NHP retina at 6 months post-injection. Total number of parafovea recorded cells displaying or not light responses in primate retinas injected either with AAV2-CMV-hCatCh (left) or AAV2-SNCG-hCatCh (right) at a concentration of $5 \times 10^{11}$ vg per eye, 6 months post-injection. B) Same as A) but at concentration of $1 \times 10^{12}$ vg per eye. C) Percentage of responding cells as a function of the viral dose ($5 \times 10^{11}$ or $1 \times 10^{12}$ vg per eye) and the promoter (CMV or SNCG). D) Maximum firing frequency of RGCs responding to light at increasing intensities at 6 months post-injection. The four different groups of responsive cells are shown on the figure, representing the two promoters tested at low and high doses. E) Peak photocurrents (inward currents recorded at −60 mV) of RGCs responding to light at increasing intensities at 6 months post-injection. The two curves represent the two promoters tested at $1 \times 10^{12}$ vg per eye.

Single Cell Recordings (Cell-Attached and Patch-Clamp) from RGCs Expressing CatCh in NHP Retina at 6 Months Post-Injection We then compared the 4 groups in terms of proportion of responsive cells (FIG. 11a-c), and maximum firing frequency (FIG. 11d) or photocurrents (FIG. 11e, with high dose only) as a function of light intensity. We found that parafovea cells recorded from animals injected with AAV2-SNCG-hCatCh had a much higher probability to be light-responsive than cells recorded from animals injected with AAV2-CMV-hCatCh, for both viral doses. Our results also indicated that the SNCG responsive-cell groups (at both doses) were more light sensitive (faster firing activity) than groups with the CMV promoter.

Figure 12:
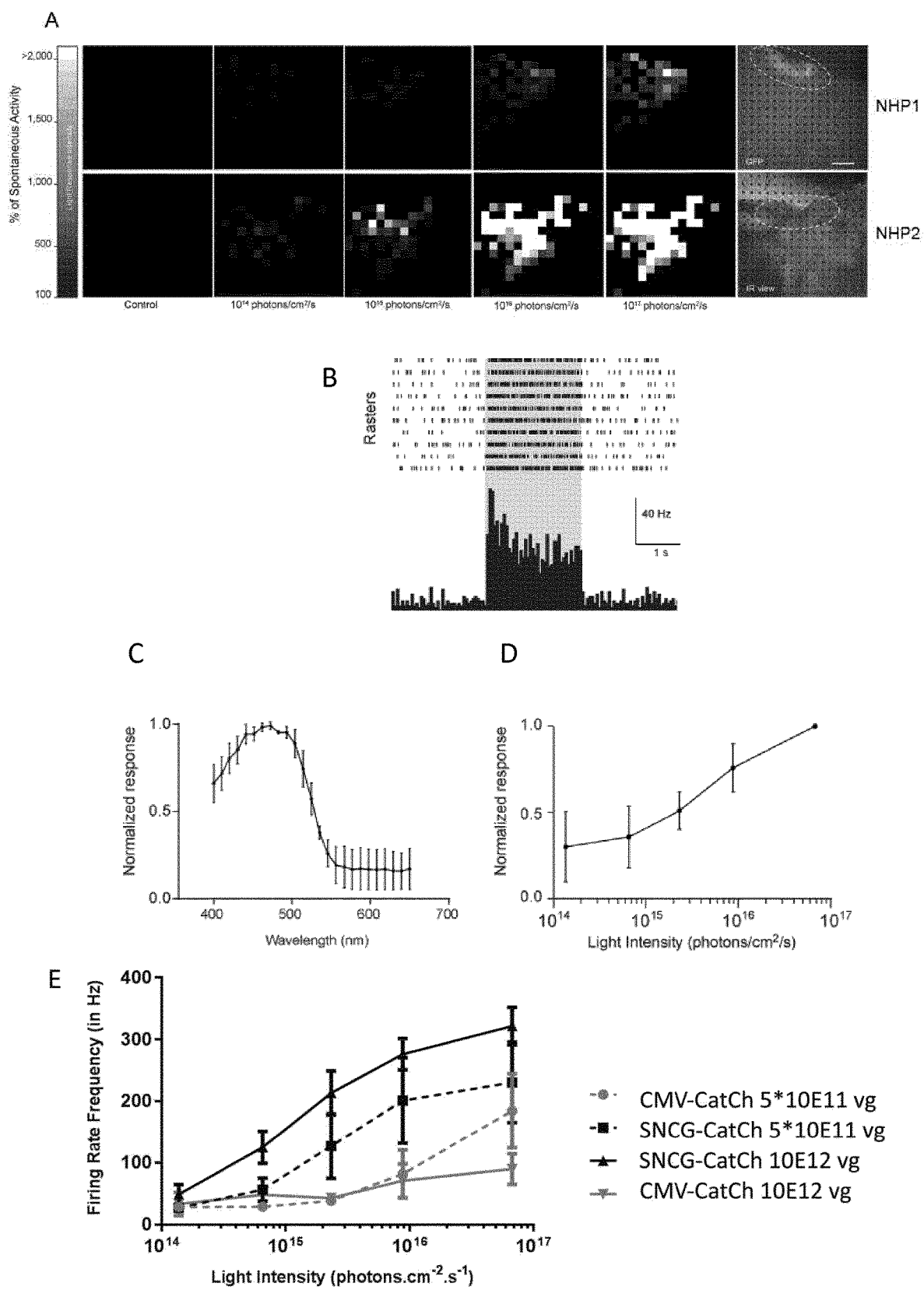
FIG. 12. MEA recordings from RGCs expressing CatCh in NHP retinas at 3 and 6 months post-injection. A) Gray scale maps based on firing rates of responding neurons (expressed as a percentage of their spontaneous activity) at increasing light intensities in primate retinas injected with AAV2-SNCG-hCatCh-GFP (top) and AAV2-SNCG-hCatCh (bottom) at a $5 \times 10^{11}$ vg per eye, 3 months post-injection. The macular area is indicated by dashed ellipses in the pictures. B) Raster plot and peri-stimulus time histogram of ganglion cell responses to full field flashes at 480 nm, after application of L-AP4 in primate retina injected with AAV2-SNCG-hCatCh-GFP. C) Average spectral tuning at $10^{17}$ photons/cm$^2$/s after application of L-AP4 in primate retinas expressing hCatCh. D) Average normalized response to different stimulus intensities. E) Discharge frequency of RGCs responding to light at increasing intensities at 6 months post-injection. Each line represents discharge frequencies normalizied across n=2 retinas for high dose group and n=3 retinas for low dose group.

Functional Responses from CatCh-Expressing RGCs Measured by Multi-Electrode Array (MEA) Recordings of the NHP Retina To define how these photocurrents control RGC activity at the population level, retinal flatmount were recorded with the multielectrode array (MEA) technique. FIG. 12b illustrates raster plots from a single unit recording of NHP1 left eye (high dose). Light responses correlated with the perifoveaolar GFP expression pattern seen on the retinal flatmount (FIG. 12a-d). No responses were obtained from the contralateral eye injected with a 5-fold lower dose. We next sacrificed other animals injected with high dose AAV2-hCatCh with no GFP tag. All of the four retinas from the high-dose group showed similar light responses under L-AP4 block with up to 90% of recorded RGCs responding to light (FIG. 12a). Similarly, the distribution of light-responsive cells was always centered on the foveolar region even with the AAV2-SNCG-hCatCh vector. These results indicate that the GFP tag is not required to obtain functional CatCh expression in RGCs. Spectral tuning of the firing frequency was calculated and showed highest frequency responses to 480 nm light, which corresponds to the excitation peak of ChR2. Firing rate frequency of responsive cells was intensity dependent with the maximum reached at the maximum light intensity applied at $10^{17}$ photons/cm$^2$/s (FIG. 12d).

In the low-dose group, only 2 out of 5 recorded retinas showed optogenetic light responses and less than 10% of recorded RGCs responded to light in those retinas. Other retinas showed spontaneous RGC activity but no light responses under L-AP4. These results indicate that $10^{11}$ particles are at the threshold where we can expect reliable optogenetic activation of RGCs through expression of CatCh.

At 6 months post injection, expression of CatCh in RGCs was comparable to responses at 3 months. CatCh-mediated light responses were observed in all tested retinas. Discharge frequency during light responses was higher in the tissues infected with the AAV2-SNCG-hCatCh vector compared to retinas infected with AAV2-CMV-hCatCh at intensities ranging from $1.10^{14}$ to $1.10^{17}$ photons·cm-2·s-1 (FIG. 12e). The threshold to trigger light responses was lower in SNCG retinas ($6.10^{14}$ and $8.10^{15}$ photons·cm-2·s-1 respectively). In the SNCG tissues, the discharge frequency at all intensities was also correlated with the dose of viral particles, the tissue with the higher viral dose showing the strongest responses. These results collectively indicate the SNCG promoter is more efficient in driving CatCh expression in macaque retinal ganglion cells compared to CMV promoter, allowing stronger light responses at dimmer light levels.

At 6 months post injection, expression of CatCh in RGCs was comparable to responses at 3 months. CatCh-mediated light responses were observed in all tested retinas. Discharge frequency during light responses was higher in the tissues infected with the AAV2-SNCG-hCatCh vector compared to retinas infected with AAV2-CMV-hCatCh at intensities ranging from 1.10E14 to 1.10E17 photons·cm-2·s-1. The threshold to trigger light responses was lower in SNCG retinas (6.10E14 and 8.10E15 photons·cm-2·s-1, respectively). In the SNCG tissues, the discharge frequency at all intensities was also correlated with the dose of viral particles, the tissue with the higher viral dose showing the strongest responses. These results collectively indicate the SNCG promoter is more efficient in driving CatCh expression in macaque retinal ganglion cells.

Example 7

Strong, RGC-Specific Expression in Primate Retina Using the Promoter Sequence of SEQ ID NO:1

This vector consists of an AAV capsid variant AAV2-7m8 (Dalkara et al., Sci Trans Med, 2013 Jun. 12; 5(189):189ra76) optimized for retinal transduction encapsidating the coding sequence of ChrimsonR-tdTomato (Klapoetke et al., Nat Methods, 2014 March; 11(3):338-46) under the control of SNCG promoter (SEQ ID NO: 1).

Four non-human primates were chosen based on absence of neutralizing antibody titers against AAV2 in their blood sera (Kotterman et al. Gene Ther. 2015 February; 22(2):116-26). Four of these adult macaques were injected intravitreally with either $5\times10^{11}$ particles of AAV2-7m8 encoding ChrimsonR-tdTomato under SNCG promoter (Table 2).

TABLE 2

Injections in non-human primates: animal number, AAV vector and viral dose injected intravitreally

| Non-human primate # | | AAV vector | Dose (vg/eye) |
|---|---|---|---|
| NHP 1 | -Right eye | AAV2-7m8-SNCG-ChrimsonR-tdTomato | $5 \times 10^{11}$ |
| | -Left eye | AAV2-7m8-SNCG-ChrimsonR-tdTomato | $5 \times 10^{11}$ |
| NHP 2 | -Right eye | AAV2-7m8-SNCG-ChrimsonR-tdTomato | $5 \times 10^{11}$ |
| | -Left eye | AAV2-7m8-SNCG-ChrimsonR-tdTomato | $5 \times 10^{11}$ |

TABLE 2-continued

Injections in non-human primates: animal number, AAV
vector and viral dose injected intravitreally

| Non-human primate # | | AAV vector | Dose (vg/eye) |
|---|---|---|---|
| NHP 3 | -Right eye | AAV2-7m8-CAG-ChrimsonR-tdTomato | $5 \times 10^{11}$ |
| | -Left eye | AAV2-7m8-CAG-ChrimsonR-tdTomato | $5 \times 10^{11}$ |
| NHP 4 | -Right eye | AAV2-7m8-CAG-ChrimsonR-tdTomato | $5 \times 10^{11}$ |
| | -Left eye | AAV2-7m8-CAG-ChrimsonR-tdTomato | $5 \times 10^{11}$ |

Figure 13:
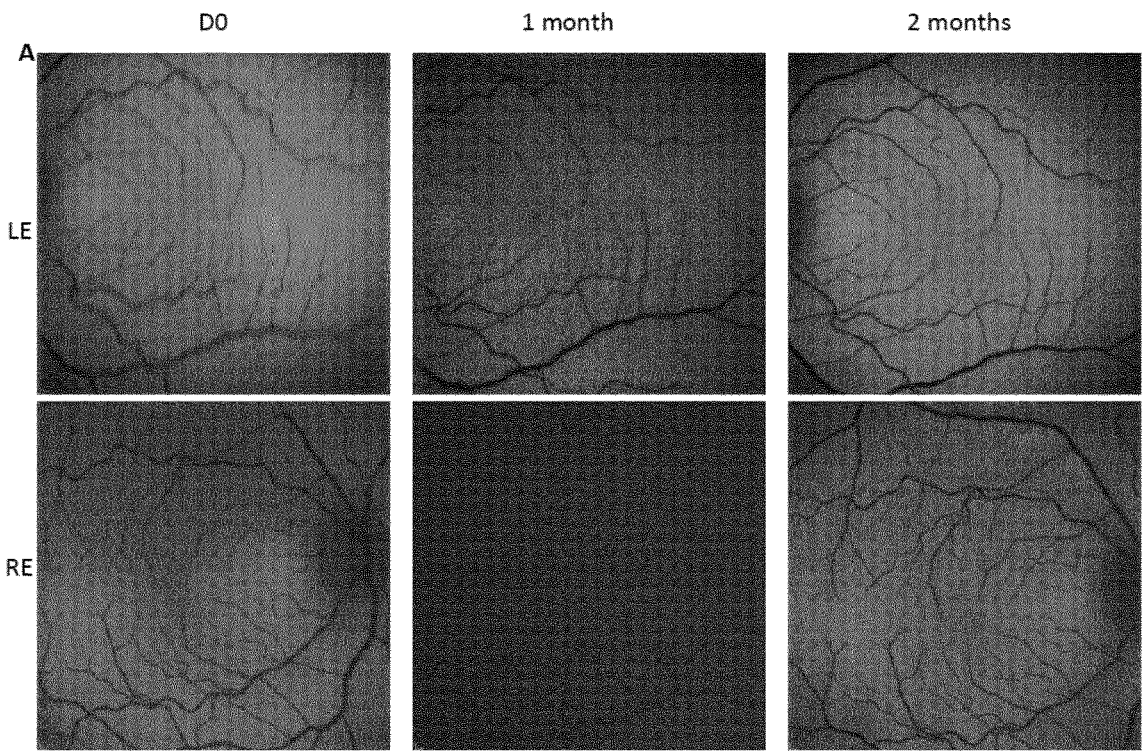
FIG. 13: Fluorescent eye-fundus images of 2 macaques injected bilaterally with AAV2-7m8-CAG-ChrimsonR-td-Tomato. Images were acquired at the day of injection, at 1 month and 2 months post-injection and do not show any detectable fluorescence at these time-points. LE: left eye, RE: Right eye.
Figure 13:
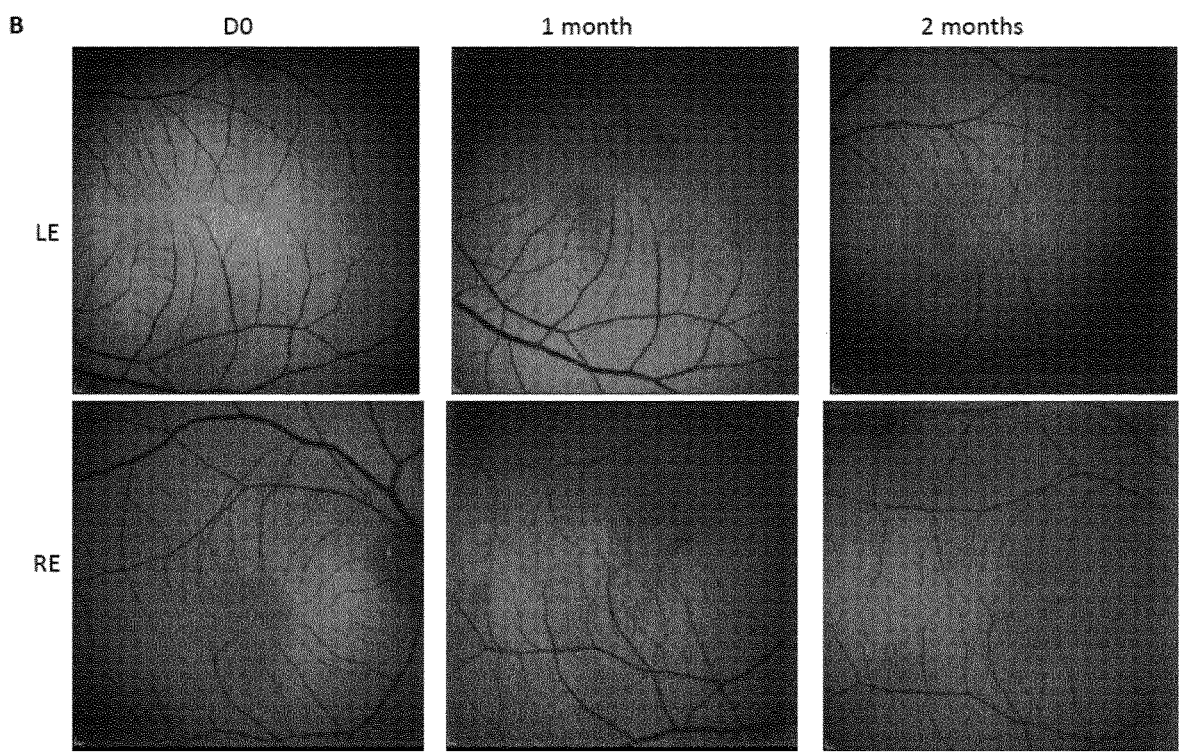
Figure 14:
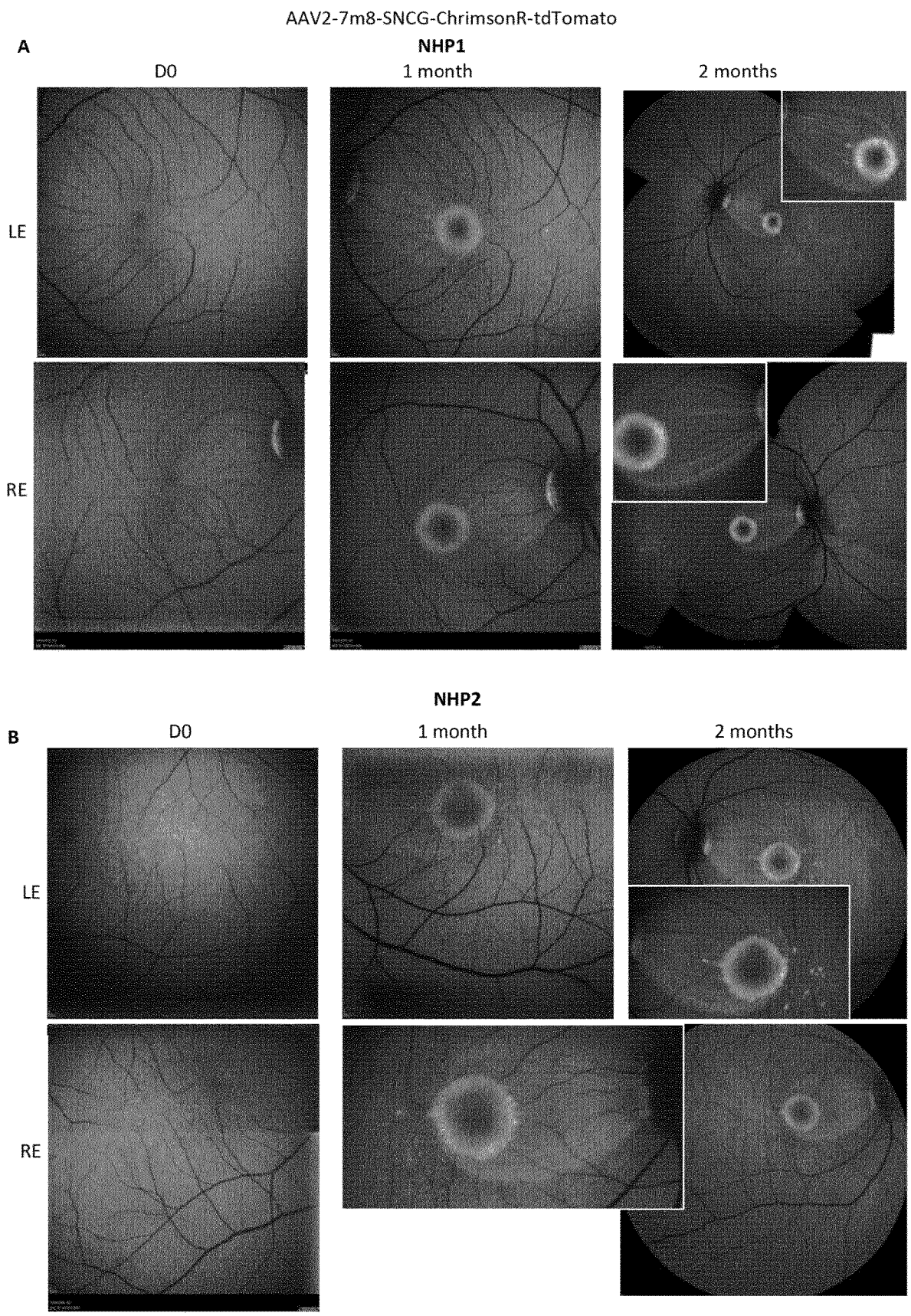
FIG. 14: Fluorescent eye-fundus images of 2 macaques injected bilaterally with AAV2-7m8-SNCG-ChrimsonR-td-Tomato. Images were acquired at the day of injection, at 1 month and 2 months post-injection show strong fluorescence (white) associated with Chrimson-tdTomato starting at 1 month post-injection. LE: left eye, RE: Right eye.

NHPs were followed for two months with fundus fluorescence. Fluorescent fundus images showed higher fluorescence in all eyes injected with SNCG promoter with respect to eyes injected with CAG promoter (FIGS. 13 and 14). ChrimsonR-tdTomato expression extending far into the periphery is clearly visible in the right eye of NHP2, as well as the other eyes.

Figure 15:
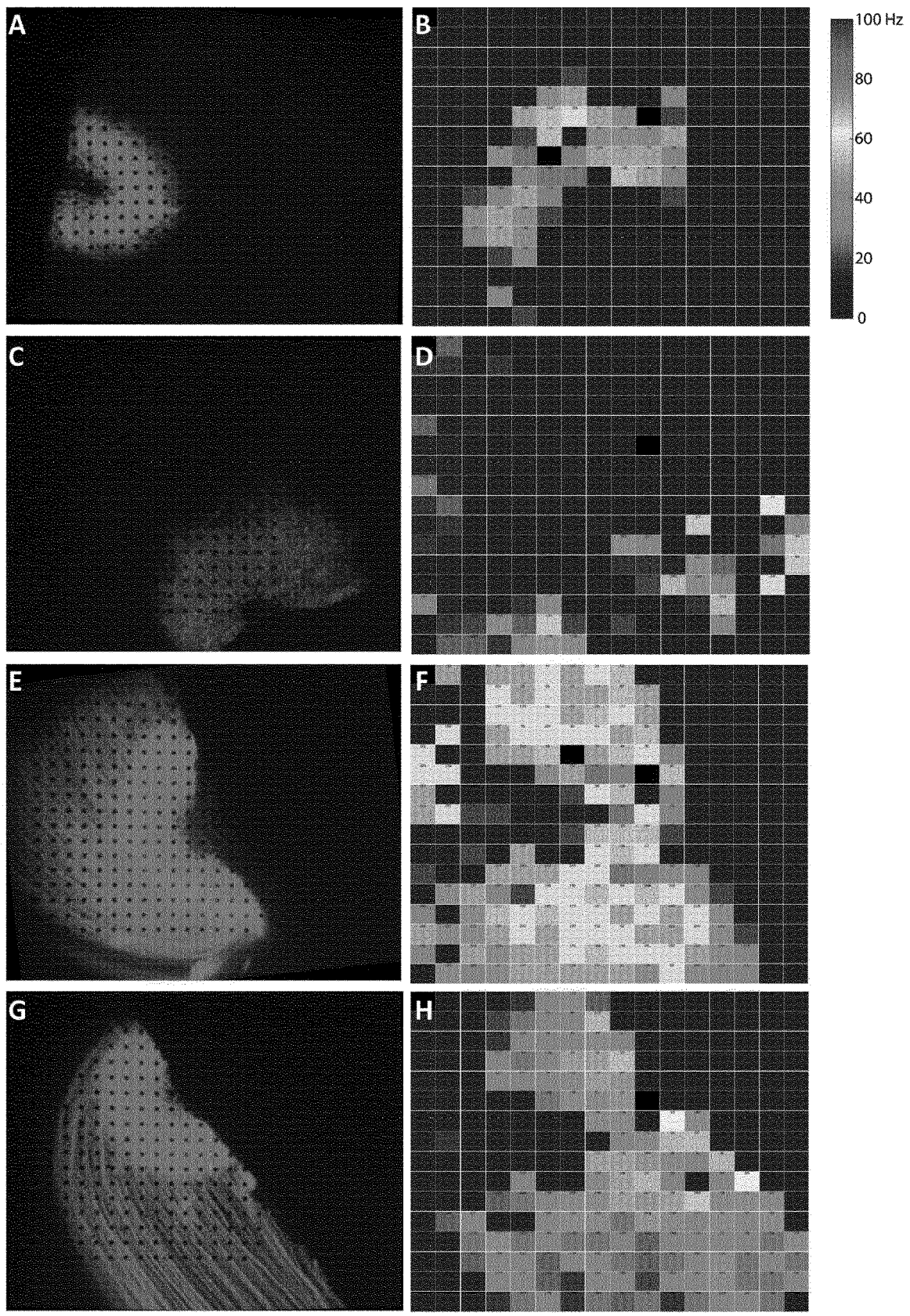
FIG. 15. A-C-E-G Images of primates semi-fovea on the multielectrode array for CAG promoter (A & C) and SNCG promoter (E & G), black dots are due to the electrode array (spacing 100 pm). B-D-F-H Gray-scale coded responses to a 10 msec full field stimulus (intensity: ×10$^{17}$ photons·cm$^2$·sec$^{-1}$) for all recording sites, for CAG (B & D) and SNCG (F & H) promoters. Same gray scale used for all representations.

Functional Responses from ChrimsonR-Expressing RGCs Measured by Multi-Electrode Array (MEA) Recordings of the NHP Retina To demonstrate that selective RGC targeting of ChrimsonR-tdTomato can restore visual function in primates, we recorded spiking activity from retinal ganglion cells using a multi-electrode array (MEA). MEA recordings were performed 6 months after injection (FIG. 15).

Color-coded response images were generated using MCRack software and represent activity at the different recording electrodes. Frequency is calculated based on the number of spikes present in a 300 ms time window including a 10 msec full field flash ($2 \times 10^{17}$ photons·cm$^2$·sec-1 at 600+/−20 nm). Spikes are detected following a 200 Hz high pass 2nd order butterworth filtering, and a thresholding on the resulting filtered signal at 20 µV. The same parameters are used for all electrodes in all the different retina pieces. Images of the ChrimsonR-tdTomato fluorescence on the MEA recording grid confirmed that the expression of ChrimsonR was obtained in a larger area under the SNCG promoter (SEQ ID NO: 1) than with the unspecific CAG promoter. In addition, the spiking activity in RGCs was also recorded in a wider area for the SNCG promoter (SEQ ID NO: 1) than for the CMV promoter. This experiment provide evidence for the optogenetic activation of a larger field with the SNCG promoter than with the CAG promoter.

Figure 16:
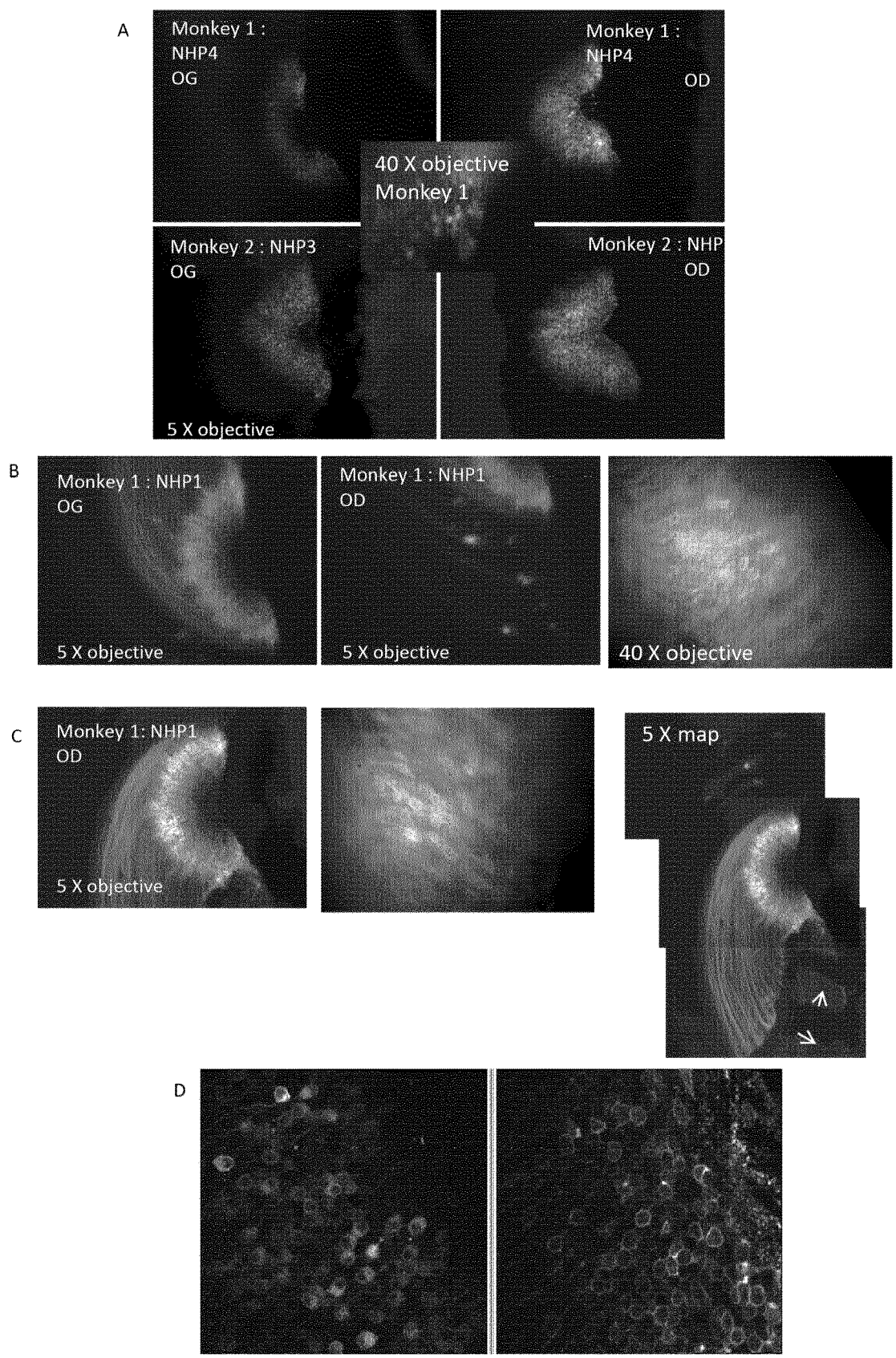
FIG. 16. Images of native fluorescence of primates semi-fovea observed with epifluorescence (A-B-C) and 2-photon microscopy (D). A) CAG promoter: images from two primates left and right semi-foveas (top, NHP4 primate; bottom, NHP3 primate) at different magnifications. B) SNCG promoter: images from NHP1 primate left semi-fovea at different magnifications and an area in the periphery of the fovea showing fluorescent spots of ChrimsonR-tdTomato expression. C) Same as B) but with NHP1 primate right semi-fovea (arrows represent. D) Representative live two-photon images from two monkeys parafoveas with two different promoters (left, CAG; right, SNCG).

All macaque retinas were imaged before single-cell electrophysiological experiments. Half of the foveal pieces were placed in the recording chamber of the microscope, with ganglion cells facing up, in oxygenated (95% O2/5% CO2) Ames medium (Sigma-Aldrich) at 36° C. for the duration of the experiment. For epifluorescence or live 2-photon imaging (FIG. 16), acquisition of td-tomato fluorescence was performed using a td-tomato filter and a CCD camera (Hamamatsu Corp., Bridgewater, N.J.) or using the 2-photon laser excitation at a wavelength of 1030 nm, respectively. 5× and 40× magnification objectives were used. These fluorescent observations further confirm the wider expression of ChrimsonR-tdTomato under the SNCG promoter than under the CAG promoter, they even show that expression outside the perifoveal ring can be obtained with the SNCG promoter as indicated by fluorescent spots (FIG. 15b). Finally, under two photon microscopy, the location of ChrimsonR-tdTomato appears to be restricted to the plasma membrane with the SNCG promoter (FIG. 15d—right).

The invention claimed is:

1. An expression cassette comprising a nucleic acid having a promoter activity in retinal ganglion cells operably linked to a nucleic acid encoding a polypeptide or nucleic acid of interest, wherein said nucleic acid having promoter activity has a length of less than 1.0 kb and comprises SEQ ID NO: 1 or a functional variant thereof having at least 90% identity to SEQ ID NO:1.

2. The expression cassette of claim 1, wherein said nucleic acid having promoter activity has a promoter activity specific to retinal ganglion cells.

3. The expression cassette of claim 1, wherein said nucleic acid having promoter activity:
   a) consists of a sequence having at least 90% identity to SEQ ID NO: 1; or
   b) consists of SEQ ID NO: 1.

4. The expression cassette of claim 1, wherein said nucleic acid having a promoter activity is operably linked to a nucleic acid encoding a polypeptide of interest.

5. The expression cassette of claim 4, wherein the polypeptide of interest is a therapeutic protein, an optogenetic actuator or a reporter protein.

6. The expression cassette of claim 5, wherein the polypeptide of interest is a therapeutic protein selected from the group consisting of NADH-ubiquinone oxidoreductase chain 4 (ND4) protein (MT-ND4), NADH-ubiquinone oxidoreductase chain 1 (ND1) protein (MT-ND1), NADH-ubiquinone oxidoreductase chain 6 (ND6) protein (MT-ND6), cytochrome b (MT-CYB), cytochrome C oxidase III (MT-CO3), NADH-ubiquinone oxidoreductase chain 5 (ND5) protein (MT-ND5), NADH-ubiquinone oxidoreductase chain 2 (ND2) (MT-ND2), cytochrome C oxidase I (MT-COI), ATP synthase Fo subunit 6 (MT-ATP6), NADH-ubiquinone oxidoreductase chain 4L (ND4L) protein (MT-ND4L), opacity-associated adhesin 1 (OPA1), opacity-associated adhesin 3 (OPA3), opacity-associated adhesin 7 (OPA7), aconitase 2 (ACO2), a neurotrophic factor, glial cell line-derived neurotrophic factor (GDNF), ciliary neuroTrophic factor (CNTF), fibroblast growth F=factor 2 (FGF2), brain-derived neurotrophic factor (BDNF), erythropoietin (EPO), an anti-apoptotic protein, B-cell lymphoma 2 protein (BCL2), BCL2-like 1 protein (BCL2L1), an anti-angiogenic factor, endostatin, angiostatin, soluble Fms-like tyrosine kinase-1 (sFlt), an anti-inflammatory factor, interleukin 10 (IL10), interleukin 1 receptor type 1 (IL1R1), transforming growth factor beta-induced (TGFBI), interleukin 4 (IL4), and rod-derived cone viability factor (RdCVF).

7. The expression cassette of claim 5, wherein the polypeptide of interest is an optogenetic actuator and is:
   a) an optogenetic activator, rhodopsin, photopsin, melanopsin, pinopsin, parapinopsin, VA opsin, peropsin, neuropsin, encephalopsin, retinochrome, RGR opsin, microbial opsin with red-shifted spectral properties, ReaChR, Chrimson, ChrimsonR, vertebrate opsin that can recruit Gi/o signalling, short wavelength vertebrate opsin, long wavelength vertebrate opsin, and channelrhodopsins from microalgae of the genus *Chlamydomonas*, channelrhodopsin-1, channelrhodopsin-2, or variant thereof; or
   b) an optogenetic inhibitor, halorhodopsin, halorhodopsin (NpHR), enhanced halorhodopsin red-shifted halorhodopsin Halo57, archaerhodopsin-3 (AR-3), archaerhodopsin (Arch), bacteriorhodopsin, enhanced bacteriorhodopsin (eBR), proteorhodopsin, xanthorhodopsin, *Leptosphaeria maculans* fungal opsin (Mac), and the cruxhalorhodopsin Jaws, or variant thereof.

8. The expression cassette of claim 5, wherein the polypeptide of interest is a reporter protein selected from the group consisting of fluorescent proteins, calcium indicators, alkaline phosphatases, beta-galactosidases, beta-lactamases, horseradish peroxidase, and variants thereof.

9. The expression cassette of claim 1, wherein said nucleic acid having a promoter activity is operably linked to a nucleic acid encoding a siRNA, an shRNA, an RNAi, an miRNA, an antisense RNA, a ribozyme and a DNAzyme.

10. The expression cassette of claim 1, wherein the polypeptide of interest is not SNCG protein.

11. The expression cassette of claim 1, wherein the polypeptide of interest is not luciferase.

12. A vector comprising the expression cassette of claim 1.

13. The vector of claim 12, wherein said vector is a viral vector.

14. The vector of claim 13, wherein said viral vector is selected from the group consisting of Moloney murine leukemia virus vectors (MoMLV), MSCV, SFFV, MPSV, SNV, lentiviral vectors, human immunodeficiency virus (HIV), simian immunodeficiency virus (SIV), feline immunodeficiency virus (Hy), bovine immunodeficiency virus (BIV), equine infectious anemia virus (EIAV), adenoviral (Ad) vectors, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors and Rous sarcoma virus vectors.

15. The vector of claim 13, wherein said viral vector is a retroviral vector, a lentiviral vector or a non-pathogenic parvovirus.

16. The vector of claim 12, wherein said vector is an adeno-associated viral (AAV) vector.

17. A viral particle comprising the vector of claim 12.

18. An AAV particle comprising the vector of claim 16 and an AAV-derived capsid.

19. The AAV particle of claim 18, wherein the AAV-derived capsid is selected from the group consisting of AAV-2, AAV-5, AAV2-7m8, AAV-9 and AAV-8 serotype capsid.

20. A cell transformed with the expression cassette of claim 1.

21. The cell of claim 20, which is a retinal ganglion cell.

22. A pharmaceutical composition comprising the expression cassette of claim 1 or a vector, viral particle, or cell comprising said expression cassette.

23. A method of treating an ocular disease comprising administering the expression cassette of claim 1 or a vector, viral particle, or cell comprising said expression cassette to a subject having an ocular disease.

24. The method of claim 23, wherein the ocular disease is a disease associated with retinal ganglion cell degeneration or photoreceptor cell degeneration.

25. The method of claim 24, wherein the ocular disease is:
  a) a disease associated with retinal ganglion cell degeneration and is selected from the group consisting of a hereditary optic neuropathy, compressive optic neuropathy, autoimmune optic neuropathy, diabetic retinopathy, glaucomatous optic nerve disease, arteritic ischemic optic neuropathy, nonarteritic ischemic optic neuropathy, infiltrative optic neuropathy, infectious optic neuropathy, optic neuritis from demyelinating disease, posradiation optic neuropathy and acrodermatitis enteropathica;
  b) a hereditary optic neuropathy, Leber's hereditary optic neuropathy, a dominant optic atrophy, optic atrophy 1, optic atrophy 3 or optic atrophy 7; or
  c) a disease associated with photoreceptor cell degeneration selected from the group consisting of age-related macular degeneration, Leber's hereditary optic neuropathy, cone-rod dystrophy, Leber congenital amaurosis, Stargardt's disease, diabetic retinopathy, retinal detachment, Best's disease, retinitis pigmentosa, choroideremia and a tapetoretinal degeneration.

26. A method of expressing a polypeptide or nucleic acid of interest in retinal ganglion cells, comprising introducing the expression cassette of claim 1 or a vector or viral particle comprising said expression cassette in retinal ganglion cells.

27. The method of claim 24, wherein the ocular disease is glaucoma.

28. The expression cassette of claim 1, wherein said nucleic acid having promoter activity has a length of less than 1.0 kb and comprises SEQ ID NO: 1.

* * * * *

UNITED STATES PATENT AND TRADEMARK OFFICE
CERTIFICATE OF CORRECTION

PATENT NO. : 11,390,866 B2  
APPLICATION NO. : 15/781191  
DATED : July 19, 2022  
INVENTOR(S) : Deniz Dalkara et al.

Page 1 of 1

It is certified that error appears in the above-identified patent and that said Letters Patent is hereby corrected as shown below:

In the Specification

Column 2,
Line 26, "Miller" should read --Müller--.

Column 8,
Line 23, "100pm)." should read --100µm).--.

Column 10,
Line 37, "2005)." should read --2005)).--.

Column 27,
Line 64, "or Miller" should read --or Müller--.

In the Claims

Column 39,
Line 10, "virus (Hy)," should read --virus (FIV),--.

Signed and Sealed this
Eighteenth Day of April, 2023

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 953
<212> TYPE: DNA
<213> ORGANISM: Homo sapiens

<400> SEQUENCE: 1

```
cacccacaag ccagttcctg tccctgagga cttggctcag ggactctggg aatgtggtag      60
acatggggtg gccccaccaa atgcatcctt atgggaacct gctccctggg agccatgaaa     120
agagcgtgga cttcgaggtg gggccacagg aagtggtcag gtccatctca ggggacctgc     180
tgcccatcca cactgctggc caggaaatgg ggggcaattc atgcctcctc agcaccttca     240
gcactgggcg gctcaaagaa ggcaagggac tattctgggg tcacacagca tgcagccaga     300
ggccaaggca tgaggaagtc cttcatttcc ccaccccac ccacctcaga tcctccaacc     360
ggtttcatgg cagcccaggg tccagcggca tccaggatgc tggtgggtag ctgcacagcc     420 caggccgcg gaggttggct gctctcacct aacaggccta tgtggccctg accccctacct     480 aggaagctgg ggacaatggc caaggcgcct cccctctctg tgcctgtctg tccaggtgca     540
gcatagacac agcacccctg gggccaagag cacccagcca gggctgcccc catgggtggg     600
cagggcagta aatgaatgag ggacaggttg ggaggtggcc agcccctcc agccatgga     660 gggcacgggg caggagagct gggctgagcc agcaggagcc cagggagcct ggtctctgcc     720
ttcctatcct ggaggaaggt gaggctgaac ctccttccct ccctccctcc ctcccgcc     780 ccactgcacg cagggctggc tgggctccag ctggcctccg catcaatatt tcatcggcgt     840
```

```
caataggagg catcggggac agccgctgcg gcagcactcg agccagctca agcccgcagc    900
tcgcagggag atccagctcc gtcctgcctg cagcagcaca accctgcaca ccc           953

<210> SEQ ID NO 2
<211> LENGTH: 19
<212> TYPE: DNA
<213> ORGANISM: Artificial Sequence
<220> FEATURE:
<223> OTHER INFORMATION: Forward primer for SNCG promoter amplification

<400> SEQUENCE: 2
cacaagccag ttcctgtcc                                                  19

<210> SEQ ID NO 3
<211> LENGTH: 17
<212> TYPE: DNA
<213> ORGANISM: Artificial Sequence
<220> FEATURE:
<223> OTHER INFORMATION: Reverse primer for SNCG promoter amplification

<400> SEQUENCE: 3
gggtgtgcag ggttgtg                                                    17
```